(12) United States Patent
Dutta

(10) Patent No.: US 7,595,331 B2
(45) Date of Patent: *Sep. 29, 2009

(54) N-AND O-SUBSTITUTED 4-[2-(DIPHENYLMETHOXY)-ETHYL]-1-[(PHENYL)METHYL]PIPERIDINE ANALOGS AND METHODS OF TREATING CNS DISORDERS THEREWITH

(75) Inventor: Aloke K. Dutta, Novi, MI (US)

(73) Assignee: Wayne State University, Detroit, MI (US)

( * ) Notice: Subject to any disclaimer, the term of this patent is extended or adjusted under 35 U.S.C. 154(b) by 491 days.

This patent is subject to a terminal disclaimer.

(21) Appl. No.: 11/007,484

(22) Filed: Dec. 8, 2004

(65) Prior Publication Data

US 2005/0154021 A1 Jul. 14, 2005

Related U.S. Application Data

(63) Continuation of application No. 10/311,796, filed as application No. PCT/US01/40964 on Jun. 14, 2001, now Pat. No. 6,995,268.

(60) Provisional application No. 60/212,921, filed on Jun. 20, 2000.

(51) Int. Cl.
*A61K 31/445* (2006.01)
*C07D 211/40* (2006.01)

(52) U.S. Cl. .................. 514/327; 514/317; 514/318; 514/328; 514/331; 546/193; 546/212; 546/214; 546/216; 546/223; 546/229; 546/232

(58) Field of Classification Search ................ 514/317, 514/318, 327, 328, 331; 546/193, 212, 214, 546/216, 223, 229, 232
See application file for complete search history.

(56) References Cited

U.S. PATENT DOCUMENTS

| | | | |
|---|---|---|---|
| 5,232,929 A | 8/1993 | Desai et al. | |
| 5,300,499 A | 4/1994 | Chow | |
| 5,344,835 A | 9/1994 | Alker et al. | |
| 6,413,956 B1 * | 7/2002 | Albaugh et al. | ............. 514/220 |

FOREIGN PATENT DOCUMENTS

| | | |
|---|---|---|
| EP | 0 217 286 A | 4/1987 |
| EP | 0 417 698 A | 3/1991 |
| WO | WO 98 50534 A | 11/1998 |
| WO | WO 99 25686 | 5/1999 |

OTHER PUBLICATIONS

Tatsuki et al. "Preparation of cyclic amine . . . " CA 131:18925 (1999).*
M.J. Kuhar, "Neurotransmitter Uptake: A Tool in Identifying Neurotransmitter Specific Pathways," Life Sci., 13, 1623-34, 1973.
M.E.A. Reith et al., "Strucural Requirements for Cocaine Congeners to Interact with Dopamine and Serotonin Uptake Sites in Mouse Brain and to Induced Stereotyped Behavior," Biochem. Pharmacol., 1986, 35, 1123-1129.
M.C. Ritz et al., "Cocaine Inhibition of Ligand Binding at Dopamine, Norpinephrine and Serotonin Transporters: A Structure-Activity Study," Life. Sci., 1990, 46, 635-645.
M.C. Ritz et al., "Cocaine Receptors on Dopamine Transporters are Related to Self-Administration of Cocaine," Science, 1987, 237, 1219-1223.
B. Giros et al., "Hyperlocomotion and Indifference to Cocaine and Amphetamine in Mice Lacking the Dopamine Transporter," Nature, 1996, 379, 606-612.
H. Shoemaker et al., Naunyn Schmiedebergs Arch. Pharmacol., 1985, 329, 227-235.
J.M. Maloteaux et al., Eur. J. Pharm., 1988, 156, 331-340.
H.B. Niznik et al., Arch. Biochem. Biophys., 1990, 276, 424-432.
K. M. Johnson, "Phencyclidine: Behavioral and Biochemical Evidence Supporting a Role for Dopamine," Fed. Proc., 1983, 42, 2579-3583.
E.D. French et al., "Phencyclidine Binding Sites in the Nucleus Accumbens and Phencyclidine-Induced Hyperactivity are Decreased Following Legions of the Mesolimbic Dopamine System," Eur. J. Pharmacol., 1985, 116, 1-9.
J. Langston et al., "MPTP: Current Concepts and Controversies," Clin. Neuropharmac., 1986, 9, 485-507.
H. Kinemuchi et al., "The Neurotoxicity of 1-methyl-4-phenyl-1,2,3,6-tetrahydropyridine (MPTP) and its Relevance to Parkinson's Disease." Neurochem. Int., 1987, 11, 359-373.
F.I. Carroll et al., "Cocaine Receptor: Biochemical Characterization and Structure-Activity Relationship of Cocaine Analogues at the Dopamine Transporter," J. Med. Chem., 1992, 35, 969-981.
R.A. Millius et al., "Synthesis and Receptor Binding of N-substituted Tropane Derivatives," " High Affinity Ligands for Cocaine Receptor," J. Med. Chem., 1991, 34, 1728-1731.
I. Chaudieu et al., "Role of the Aromatic Group in the Inhibition of Phencyclidine Binding and Dopamine Uptake by PCP Analogs," Pharmacol. Biochem. Behav., 1989, 32, 699-705.
J. Vignon et al., "[$^3$H]N-[1(2-Benzo(b)thienyl)cyclohexyl]piperidine( [$^3$H]BTCP) : A New Phencyclidine Analog Selective for the Dopamine Uptake Complex," Eur. J. Pharmacol., 1988, 148, 427-436.
P.H. Anderson, "Biochemical and Pharmacological Characterization of [$^3$H]GBR 12935 Binding in Vitro to Rat Striatal Membranes: Labeling of the Dopamine Uptake Complex," J. Neurochem., 1987, 48, 1887-1896.
P.H. Anderson, "The Dopamine Uptake Inhibitor GBR 12909: Selectivity and Molecular Mechanism of Action," Eur. J. Pharmacol., 1989, 166, 493-504.

(Continued)

*Primary Examiner*—Celia Chang
(74) *Attorney, Agent, or Firm*—Brooks Kushman P.C.

(57) ABSTRACT

N- and O-substituted 4[2-diaromaticmethoxy and methylamino)alkyl]piperidines exhibit high CNS activity with respect to the dopamine transporter (DAT) and serotonin transporter (SERT). Preferred compounds exhibit highly differential behavior as between the DAT and SERT and between the DAT and the norepinephrine transporter (NET). The compounds have utility in treating CNS disorders, including but not limited to cocaine addiction, depression, and Parkinson's disease.

11 Claims, 4 Drawing Sheets

OTHER PUBLICATIONS

R.B. Kolhatkar et al., "Interaction of *cis*- (6-Benzhydrylpiperidin-3-y)benzylamine Analogues with Monoamine Transporters: Structure-Activity Relationship Study of Structurally Constrained 3,6-Disubstituted Piperidine Analogues of (2,2-Diphenylethyl) - (1-(4-fluorobenzyl) piperidin-4-ylmethyl)amine," J. Med. Chem. 2003, 46, 2205-2215.

C. DeVries et al., "Heteroaromatic Analogs of 1-2[2-(diphenylmethoxy(ethyl] - and 1-[2(bis(4-fluorophenyl) methoxy]ethyl) -4- (3-phenylpropyl) piperazines (GBR 12935 and GBR 12909) as High-Affinity Dopamine Reuptake Inhibitors," J. Med. Chem., 1997, 40, 705-716.

D. Matecka et al., Development of Novel; Potent, and Selective Dopamine Reuptake Inhbitors Through Alteration of the Piperazine Ring of 1- [2-(diphenylmethoxy)ethyl] - and 1[2-[Bis (4-fluorophenyl)methoxy]ethyl] -4-(3-phenylpropyl) piperazines (GBR 12935 and GBR 12909), J. Med. Chem., 1996, 39, 4704-4716.

R.B. Rothman, "Tight Binding Dopamine Reuptake Inhibitors as Cocaine Antagonists," FEBS Lett., 1989, 257, 341-344.

U. Sogaard et al., "A Tolerance Study of Single and Multiple Dosing of the Selective Dopamine Uptake Inhibitor GBR 12909 in Healthy Subjects," Int. Clin. Psychopharm., 1990, 5, 237-251.

J.R. Glowa et al., "The Effects of GBR 12909 on Responding of Rhesus Monkeys Maintained Under Schedules of Cocaine- and Food-Delivery," NIDA. Res. Monogr., 1994, 141, 12.

A.K. Dutta et al., "Positional Importance of the Nitrogen Atom in Novel Piperidine Analogs of GBR 12909: Affinity and Selectivity for the Dopamine Transporter," Med. Chem. Res., 1993, 3, 209-222.

A.K. Dutta et al., "Structure-Activity Relationship Studies of Novel 4[2-[Bis(4-fluorophenyl)methoxy]ethyl] -1-(3-phenylpropyl)piperidine Analogs: Synthesis and Biological Evaluation of the Dopamine and Serotonin Transporter Sites," J. Med. Chem., 1996, 39, 749-756.

A.K. Dutta et al., "Highly Selective, Novel Analogs of 4-[2-(diphenylmethoxy)ethyl]-1-benzylpiperidine for the Dopamine Transporter: Effect of Different Aromatic Substitutions on their Affinity and Selectivity," J. Med. Chem., 1997, 40, 35-43.

A.K. Dutta et al., "Potent and Selective Ligands for the Dopamine Transporter (DATE): Structure-Activity Relationship Studies of Novel 4-[2- (diphenylmethoxy) ethyl]-1-(3-phenylpropyl) piperidine Analogs," J. Med. Chem., 1998, 41, 699-756.

M. Khalid et al., "N, N'-disubstituted L-isoglutamines as Novel Cancer Chemotherapeutic Agent," Drugs Exp. Clin. Res. (1987), 13 (Suppl. 1), 57-60; ISSN: 0378-6501, 1987.

Database WPI Section Ch., Week 9804, Derwent Publications Ltd., London, GB; Class B03, an 98-035793 XP002094912 & JP 09 249566 A (Takeda Chem. Ind. Ltd.) Sep. 22, 1997 (see abstract).

Derwent Abstract, Eur. J. Nucl. Med., (1999), 26 (4), 342-347, "In Vivo Imaging of Serotonin Transporters with [99mTc] TRODAT-1 in Nonhuman Primates" [AN 1999:164775].

A.K. Dutta et al., "Tolerance in the Replacement of the Benzhydrylic O Atom in 4-[2-(Diphenylmethoxy)ethyl]-1- benzylpiperidine Derivatives by an N Atom: Development of New-Generation Potent and Selective N-Analogue Molecules for the Dopamine Transporter," J. Med. Chem., vol. 41, No. 17, pp. 3293-3297.

F. Ivy Carroll et al., "Cocaine and 3β- (4'-Substituted phenyl)tropane-2β-carboxylic Acid Ester and Amide Analogues. New High Affinity and Selective Compounds for the Dopamine Transporter," J. Med. Chem. 1995, 38, 379-388.

Baker Botts, "In Prints-reach through claims," Attorneys Practice Profiles News & Events ( 2002).

Burger, "Medicinal Chemistry," p. 25 (1970).

Rubini et al., "Synthsis of Isosteric Methylene-oxy . . . ," Tetrahedron v. 42(21) 6039-45 (1986).

Database on STN CASDATA (Columbus, Ohio, USA) Abstract No. 132:119356, Hoepping et al., "Synthesis and biological evaluation of two novel DAT binding technetium complexes" Bioorg. Med. Chem. Lett. (1999) vol. 9, No. 22, pp. 3211-3216.

* cited by examiner

N- AND O-SUBSTITUTED 4-[2-(DIPHENYLMETHOXY)-ETHYL]-1-[(PHENYL)METHYL]PIPERIDINE ANALOGS AND METHODS OF TREATING CNS DISORDERS THEREWITH

CROSS-REFERENCE TO RELATED APPLICATIONS

This application is a continuation of U.S. application Ser. No. 10/311,796, filed Mar. 28, 2003, now U.S. Pat. No. 6,995, 268 which claims the benefit of PCT application PCT/U501/ 40964, filed Jun. 14, 2001, which claims the benefit of U.S. provisional application Ser. No. 60/212,921, filed Jun. 20, 2000.

TECHNICAL FIELD

The present invention pertains to novel pharmacologically active compounds which exhibit activity for monoamine transporter systems, specifically for the dopamine transporter ("DAT"), serotonin transporter ("SERT"), and norepinephrine transporter ("NET"). The novel compounds exhibit a high differential in activity for the DAT relative to the SERT.

BACKGROUND OF THE INVENTION

The dopamine transporter is a presynaptically located macromolecule which plays an important role in pathophysiocological processes in the central nervous system (CNS). The DAT terminates dopaminergic neurotransmission by reaccumulation of released dopamine into presynaptic neurons, M. J. Kuhar, "Neurotransmitter Uptake: A Tool in Identifying Neurotransmitter Specific Pathways", LIFE SCI., 13, 1623-34, 1973. In cocaine addiction, binding of cocaine to the DAT and consequent blockage of dopamine uptake appears to be related to the reinforcing properties of the drug. M. E. A. Reith et al., "Structural Requirements for Cocaine Congeners to Interact With Dopamine and Serotonin Uptake Sites in Mouse Brain and to Induced Stereotyped Behavior", BIOCHEM. PHARMACOL., 1986, 35, 1123-1129; M. C. Ritz et al., "Cocaine Inhibition of Ligand Binding At Dopamine, Norpinephrine and Serotonin Transporters: A Structure-Activity Study", LIFE. SCI., 1990, 46, 635-645; M. C. Ritz et al., "Cocaine Receptors On Dopamine Transporters Are Related to Self-Administration of Cocaine", SCIENCE, 1987, 237, 1219-1223; B. Giros et al., "Hyperlocomotion and Indifference to Cocaine and Amphetamine in Mice Lacking the Dopamine Transporter", NATURE, 1996, 379, 606-612. Also associated with the transport function is concentration of neurotoxic chemicals in dopaminergic neurons which is implicated in Parkinson's disease. The transporter macromolecule may be a marker for Parkinson's, H. Shoemaker et al., NAUNYN SCHMIEDEBERGS ARCH. PHARMACOL., 1985, 329, 227-235 and J. -M. Maloteaux et al., EUR. J. PHARM., 1988, 156, 331-340, as evidenced by its absence in tissue sections of Parkinson's diseased putamen. H. B. Niznik et al., ARCH. BIOCHEM. BIOPHYS., 1990, 276, 424-432 and M. J. Kaufman et al., SYNAPSE, 1991, 9, 43-49. Consequently, potent yet selective ligands for the DAT have potential for in vivo monitoring of primary targets of cocaine in the brain, for characterization of cocaine binding sites, for pharmacotherapeutic agents for treatment of cocaine addition, and for monitoring of Parkinson's Disease.

Cocaine is known to bind to various neurotransporter systems in the brain, M. E. A. Reith et al., op. cit., but the reinforcing effect of cocaine which is a factor in cocaine addition, is believed to be initiated by binding to the DAT, causing inhibition of dopamine transport. Phencyclidine (PCP), a psychoactive drug of abuse, is also known to exhibit at least some of its behavioral effects through binding to the DAT. K. M. Johnson, "Phencyclidine: Behavioral and Biochemical Evidence Supporting a Role For Dopamine", FED. PROC., 1983, 42, 2579-2583; E. D. French et al., "Phencyclidine Binding Sites in the Nucleus Accumbens and Phencyclidine-Induced Hyperactivity are Decreased Following Lesions of the Mesolimbic Dopamine System", EUR. J. PHARMACOL., 1985, 116, 1-9. The DAT further plays a crucial role in the neurotoxic action of 1-methyl-4-phenyl-1, 2,3,6-tetrahydropyridine (MPTP) which induces idiopathic Parkinson's syndrome in humans. J. Langston et al., MPTP: Current Concepts and Controversies", CLIN. NEUROPHARMAC., 1986, 9, 485-507; H. Kinemuchi et al., "The Neurotoxicity of 1-methyl-4-phenyl-1,2,3,6-tetrahydropyridine (MPTP) and its Relevance to Parkinson's Disease", NEUROCHEM. INT., 1987, 11, 359-373. The serotonin transporter (SERT) is also implicated in numerous neurological processes. For example, SERT is strongly implicated in depression and drug addiction.

Several classes of compounds have been developed to characterize cocaine and PCP binding sites at the DAT. M. E. A. Reith et al., op. cit., F. I. Carroll et al., "Cocaine Receptor: Biochemical Characterization and Structure-Activity Relationship of Cocaine Analogues at the Dopamine Transporter", J. MED. CHEM., 1992, 35, 969-981; R. A. Millius et al., "Synthesis and Receptor Binding of N-substituted Tropane Derivatives", "High Affinity Ligands For Cocaine Receptor", J. MED. CHEM., 1991, 34, 1728-1731; I. Chaudieu et al., "Role of the Aromatic Group in the Inhibition of Phencyclidine Binding and Dopamine Uptake by PCP Analogs", PHARMACOL. BIOCHEM. BEHAV., 1989, 32, 699-705. Extensive structure-activity relationship (SAR) studies of cocaine analogs resulted in the development of potent and selective tropane derivatives which bind to the DAT. Some well known compounds of this class include CFT (Win 35,428) and RTI-55. The similarity of the structures of these tropane derivatives and cocaine is readily apparent.

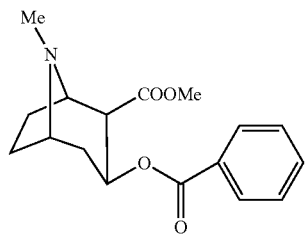

(-) Cocaine

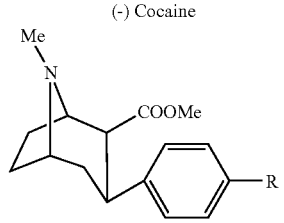

Win 35, 428, R = F
RTI-55, R = I

More recent reports describe yet more potent and selective tropanes, P. C. Meltzer et al., "Substituted 3-phenyltropane Analogs of Cocaine: Synthesis, Inhibition of Binding At Cocaine Recognition Sites, and Positron Emission Tomography Imaging", J. MED. CHEM., 1993, 36,-855-862; F. I. Carroll et al., "Cocaine and 3β-(4'-substituted phenyl)tropane-2β-carboxylic acid ester and amide analogues. New High-affinity and Selective Compounds for the Dopamine Transporter", J. MED. CHEM., 1995, 38, 379-388. In similar fashion, modification of PCP led to development of more potent analogs, I. Chaudieu et al., "Role of the Aromatic Group in the Inhibition of Phencyclidine Binding and Dopamine Uptake By PCP Analogs", PHARMACOL. BIOCHEM. BEHAV., 1989, 32, 699-705; and J. Vignon et al., "[$^3$H]N-[1-(2-Benzo(b)thienyl)cyclohexyl]piperidine([$^3$H]BTCP): A New Phencyclidine Analog Selective for the Dopamine Uptake Complex", EUR. J. PHARMACOL., 1988, 148, 427-436.

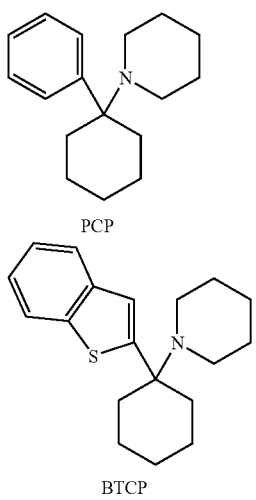

PCP

BTCP

The "GBR" class of compounds, P. Van der Zee et al., "Aryl 1,4-dialk(en)ylpiperazines as Selective and Very Potent Inhibitors of Dopamine Uptake", EUR. J. MED. CHEM, 1980, 15, 363-370, are known for their unusually high selectivity and potency for the DAT.

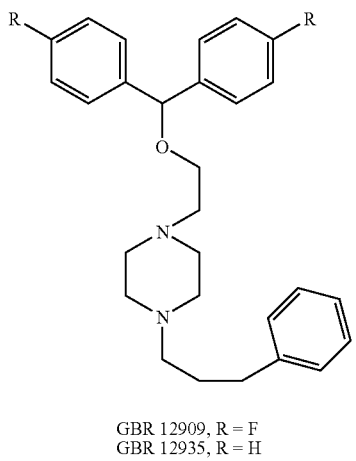

GBR 12909, R = F
GBR 12935, R = H

Two of these, with R=F and R=H, have affinities in the low nanomolar range. P. H. Anderson, "Biochemical and Pharmacological Characterization of [$^3$H]GBR 12935 Binding in Vitro to Rat Striatal Membranes: Labeling of the Dopamine Uptake Complex", J. NEUROCHEM., 1987, 48, 1887-1896; P. H. Anderson, "The Dopamine Uptake Inhibitor GBR 12909: Selectivity and Molecular Mechanism of Action", EUR. J. PHARMACOL., 1989, 166, 493-504. An extensive structure/activity relationship (SAR) study produced several very potent compounds for the DAT. C. DeVries et al., "Heteroaromatic Analogs of 1-[2-(diphenylmethoxy)ethyl]- and 1-[2-[bis(4-fluorophenyl)methoxy]ethyl]-4-(3-phenylpropyl)piperazines (GBR 12935 and GBR 12909) as High-Affinity Dopamine Reuptake Inhibitors", J. MED. CHEM., 1997, 40, 705-716; D. Matecka et al., "Development of Novel, Potent, and Selective Dopamine Reuptake Inhibitors Through Alteration of the Piperazine Ring of 1-[2-(diphenylmethoxy)ethyl]- and 1-[2-[Bis(4-fluorophenyl)methoxy]ethyl]4(3-phenylpropyl)piperazines (GBR 12935 and GBR 12909)", J. MED. CHEM., 1996 39, 4704-4716. Radiolabeling of these compounds has facilitated elucidation of neuropharmacological activity. The GBR with R=F dissociates very slowly from the DAT, R. B. Rothman, "Tight Binding Dopamine Reuptake Inhibitors as Cocaine Antagonists", FEBS LETT., 1989, 257, 341-344 and attenuates increase in extracellular dopamine levels induced by cocaine as measured by microdialysis. R. B. Rothman, op. cit.; U. Sogaard et al., "A Tolerance Study of Single and Multiple Dosing of the Selective Dopamine Uptake Inhibitor GBR 12909 in Healthy Subjects", INT. CLIN. PSYCHOPHARM., 1990, 5, 237-251. This compound was non-stimulatory in human volunteers, J. R. Glowa et al., "The Effects of GBR 12909 on Responding of Rhesus Monkeys Maintained Under Schedules of Cocaine- and Food-Delivery", NIDA. RES. MONOGR., 1994, 141, 12, and has recently been shown to block cocaine self-administration behavior in the rhesus monkey. A. K. Dutta et al., "Positional Importance of the Nitrogen Atom in Novel Piperidine Analogs of GBR 12909: Affinity and Selectivity for the Dopamine Transporter", MED. CHEM. RES., 1993, 3, 209-222. Such studies raise the possibility that suitable compounds may serve as cocaine antagonists without being themselves addictive.

SUMMARY OF INVENTION

The present invention pertains to N- and O-versions of 4-[2-diarylamino or oxoalkyl]piperidine derivatives which exhibit neuropharmacological activity with respect to the DAT, the SERT, and/or the NET. Preferred compounds of this class exhibit low nanomolar activity with respect to the DAT, and high differential binding activity with respect to the DAT compared with that for the SERT and for the NET.

DESCRIPTION OF THE PREFERRED EMBODIMENTS

Figure 1:
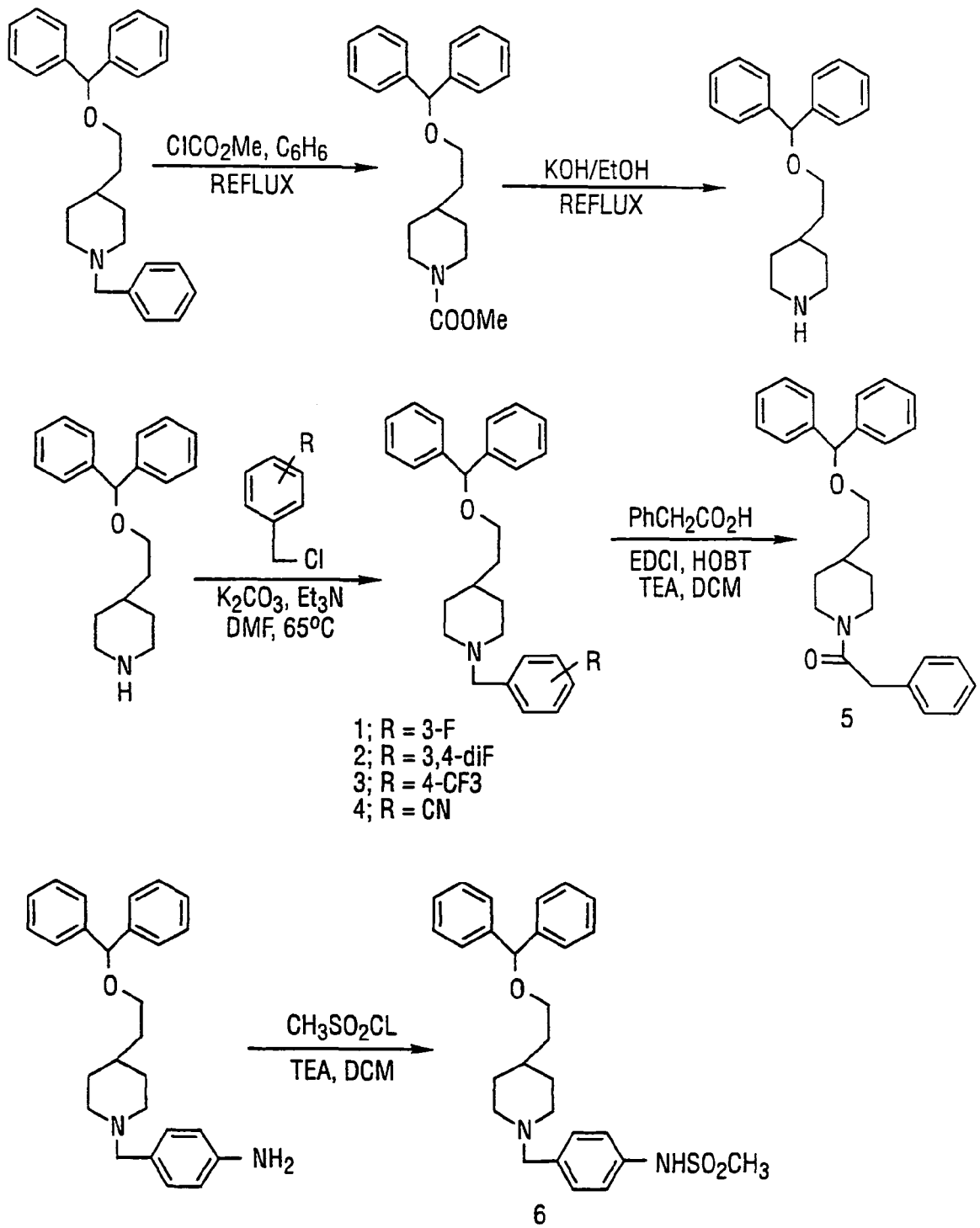
FIG. 1 illustrates one synthesis scheme and the structures of certain of the subject invention compounds.
Figure 2:
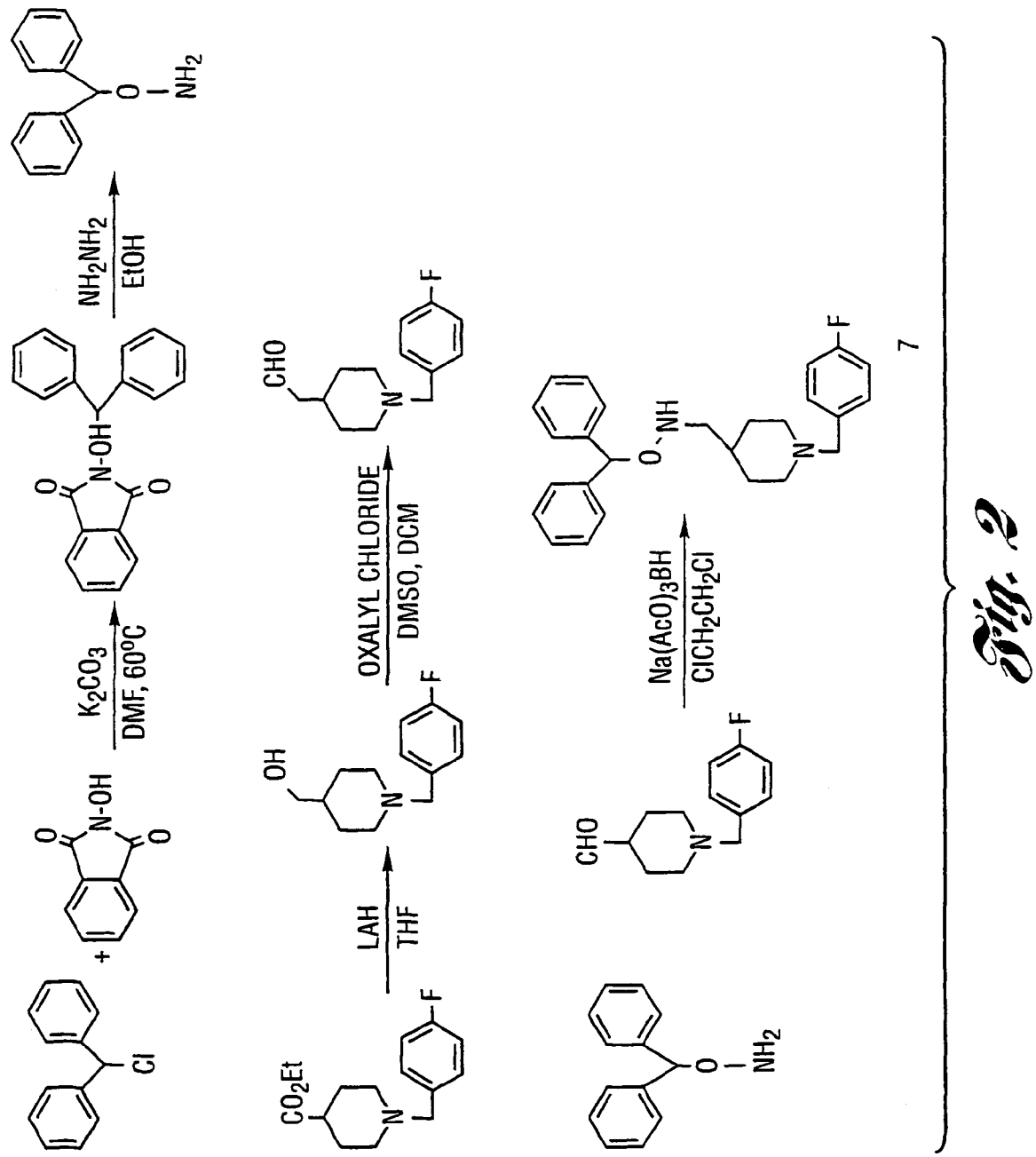
FIG. 2 illustrates a further synthesis scheme and the structures of certain of the subject invention compounds.
Figure 3:
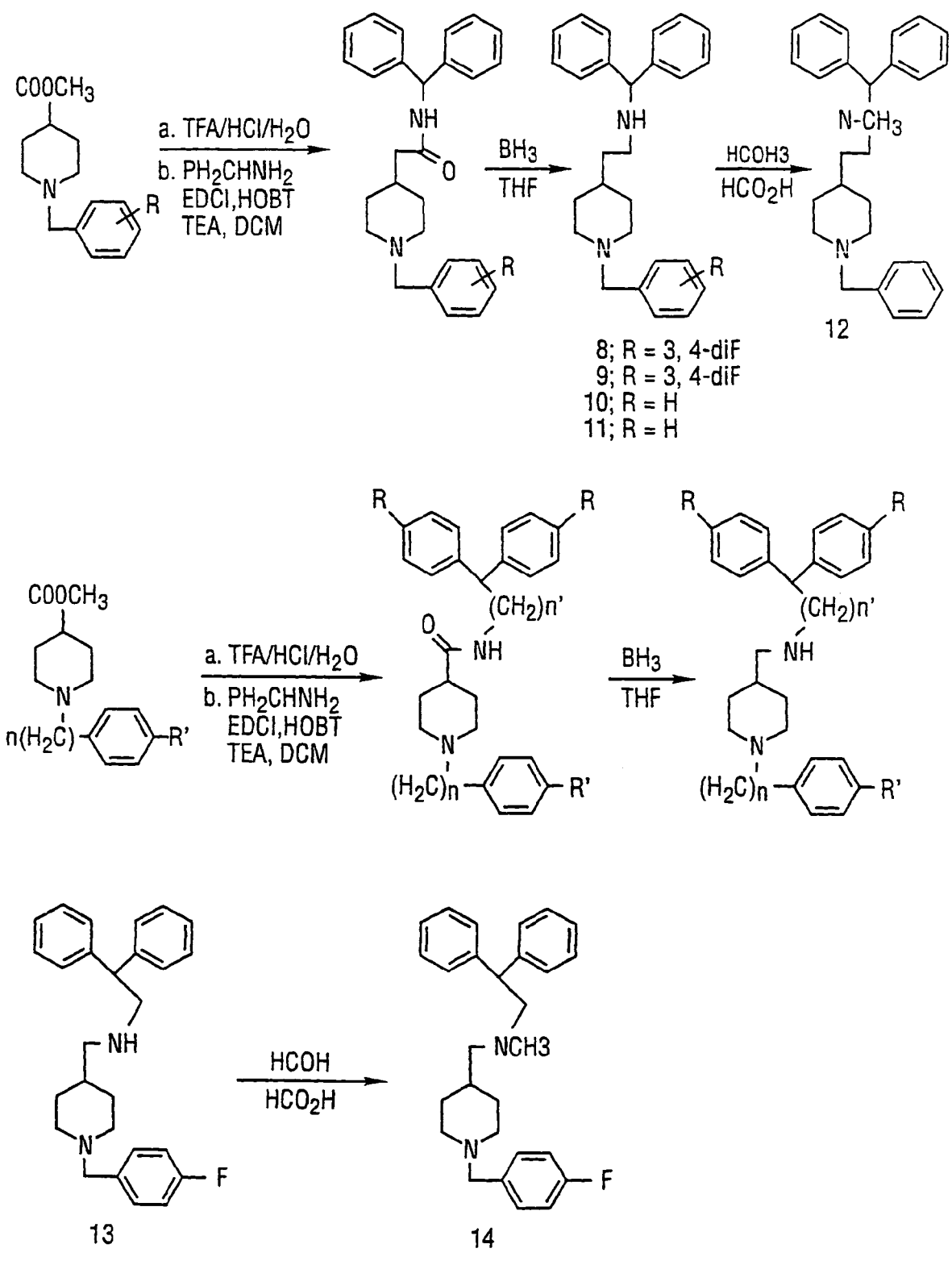
FIG. 3 illustrates a further synthesis scheme and the structures of certain of the subject invention compounds.
Figure 4:
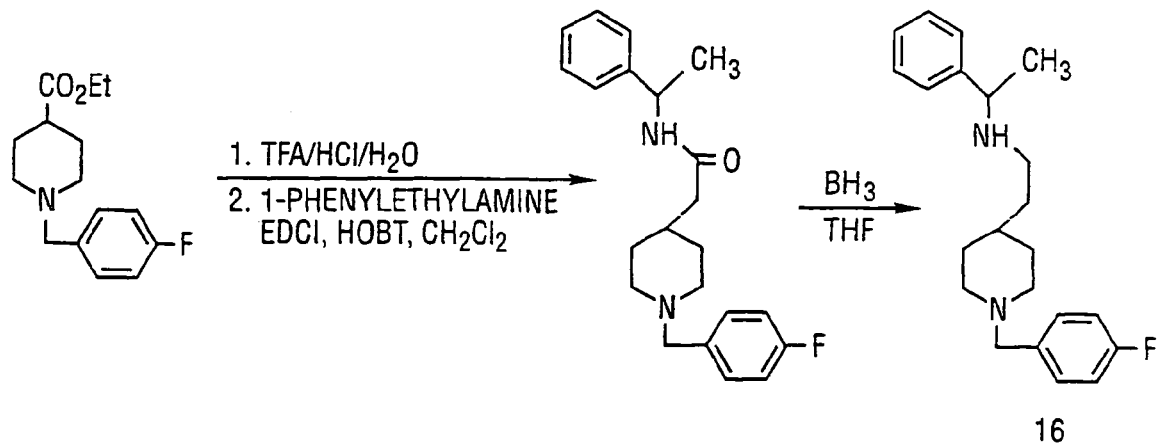
FIG. 4 illustrates a further synthesis scheme and the structures of certain of the subject invention compounds.
Figure 4:
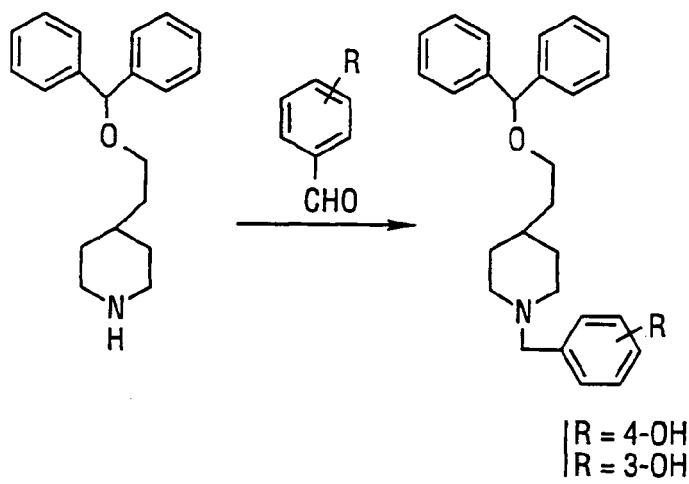

The compounds of the present invention correspond to the formula:

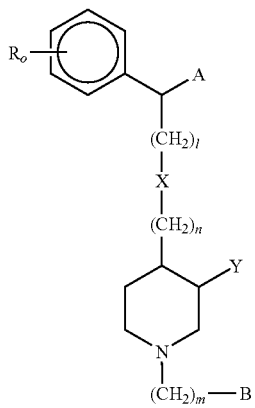

(I)

wherein A is

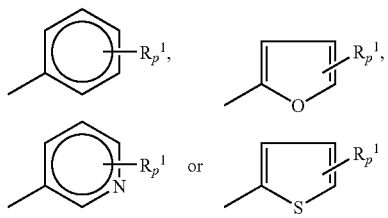

and B is

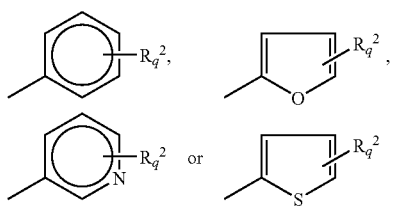

and where X is selected from the group consisting of —NH—, —NR$^4$—, —S— and —O—, R$^4$ is C$_{1-4}$ alkyl, NH$_2$, C$_{1-4}$ hydroxyalkyl, halogenated C$_{1-4}$ alkyl, C$_{2-4}$ alkenyl, C$_{2-4}$ hydroxyalkenyl, halogenated C$_{2-4}$ alkenyl, C$_{2-4}$ and alkynyl, and C$_{2-4}$ halogenated alkynyl,
Y is —H or —OH;
l is 0, 1, or 2, preferably 0 or 1, more preferably 0;
n is 1 or 2, preferably 2;
m is 1 or 2, preferably 1;
o is 0, 1, 2, 3, or 4, preferably 0, 1, or 2, most preferably 0 or 1;
p is 0, 1, 2, 3, or 4, preferably 0, 1, or 2, most preferably 0 or 1;
q is 0, 1, 2, or 3, preferably 0 or 1;
R, R$^1$, and R$^2$ are selected from the group consisting of H, F, Cl, CN, COOEt, OH, NO$_2$, NH$_2$, OR$^5$, wherein R$^5$ is C$_{1-8}$ alkyl, C$_{5-6}$ cycloalkyl, or C2-8 alkenyl or R$^2$ is a 5 or 6 membered heterocycle, preferably a heterocycle selected from the group consisting of:

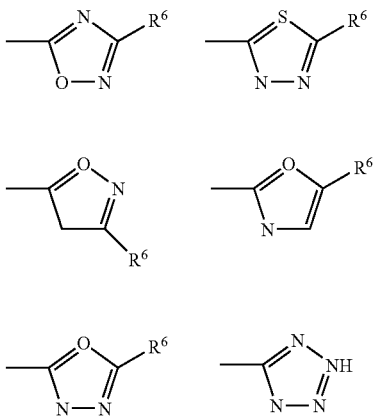

wherein R$^6$ may be C$_{1-4}$ alkyl, substituted or unsubstituted phenyl or naphthyl, it being understood that the hydroxyl group is not substituted onto an ethylenic carbon.

The compounds of the present invention also include those of the formula:

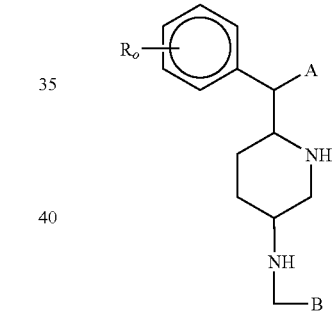

(II)

where A, B, R, and o are defined as above.

In the above formulae, A and B are preferably

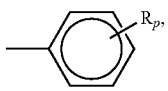

where p is 1 or 2. In the above formula, when m is 2 or 3, one of the methylene hydrogens may be substituted by OR$^7$ where R$^7$ is alkyl, preferably C$_{1-16}$ alkyl, more preferably C$_{1-4}$ lower alkyl, or C$_{2-18}$ alkylene, or

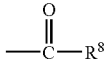

where R$^8$ is C$_{1-18}$ alkyl or C$_{2-18}$ alkylene.

Preferably, the compounds of the formula (I) correspond to

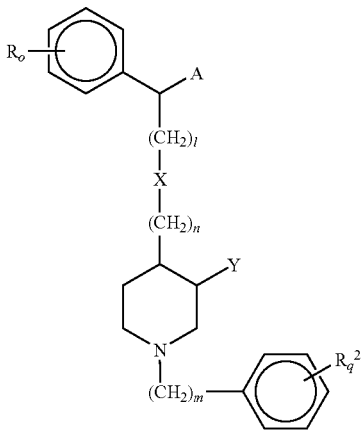

The present invention does not include compounds falling within structural Formula I or its preferred subset, when the following conditions are met:
When A is phenyl, X is O, Y is H, l is 0, m=1, and n is 1,
  R, R$^1$ and R$^2$ are not all H when B is phenyl; and
  R and R$^1$ are not both F when B is phenyl;
When A is phenyl, X is O, Y is H, 1 is 0, m=1, and n=z,
  when R$^2$ and R$^1$ are both H and B is phenyl, R$^2$ is not halo, methoxy, methyl,
  nitro, or amino when q is 1, and is not 3-chlorofluoro when q is 2;
  when R and R$^1$ are 4-fluoro, B is not an unsubstituted phenyl;
  when R is 4-halo, B is phenyl, and q is 1, R$^2$ is not F;
When A is phenyl, X is O, Y is H, 1 is 0, n is 2, m is 2, and B is unsubstituted phenyl,
  when o and p are both 1, R and R$^1$ are not both halo;
  when A is phenyl, l is 0, n is 2, and m is 2, at least one of R, R$^1$, and R$^2$ is other than H;
When A is phenyl, B is phenyl, X is O, Y is H, l is 0, m is 2, l is 2, and q is 0, R and R$^1$ are not both methyl;
When A is phenyl, X is O, Y is H, B is phenyl, l is 0, m is 2, and n is 1, not all of R, R$^1$, and R$^2$ are H,
  when r is 0 and o and p are 1, R and R$^1$ are not both 4-fluoro;
When A is phenyl, X is O, Y is H, l is 0, m is 3, and n is 2,
  when B is phenyl, q is 1, and R$^2$ is H, o and p are not both zero,
  when B is phenyl, o and p are not both 1 when R and R$^1$ are both 4-halo or are both methoxy;
When X is O, Y is H, o is 0 and A is unsubstituted phenyl, l is 0, m is 3, and n is 2, B is not 4-fluorophenyl or a 6 membered heteroaryl ring bonded to the (CH$_2$)$_m$ group at the 3-ring position;
When X is O, Y is H, A is unsubstituted thiophenyl, l is 0, m is 3, n is 2, Y is H, and B is unsubstituted phenyl, o is other than 0 but is not 1 when R is 4-fluoro;
When X is O, Y is H, A is unsubstituted thiophenyl, o is 0, l is 0, m is 1, and l is 2, B is not phenyl, 3-pyridyl, or 4(fluorophenyl).
When X is O, Y is H, A is unsubstituted phenyl, l is 0, m is 1, and n is 2, B is not unsubstituted thiophenyl or unsubstituted 2,3-benzothiophenyl.
When X is NH, Y is H, A is phenyl, l is 0, m is 1, and n is 2, when q is 0, o is 1 and p is 1, R and R$^1$ are not both 4fluoro,
  when q is 1, o is 0 and p is 0, B is not 4-(fluorophenyl).

The compounds of the present invention also include those having the structure

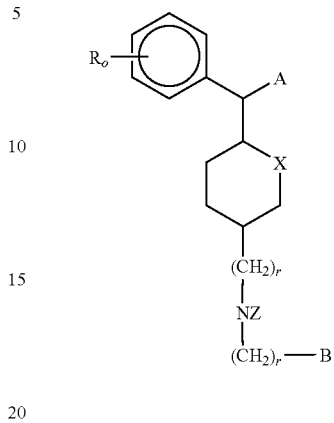

wherein A is defined as before and may also be COOCH$_3$, =O, CH$_3$, F, or OH; X is O, S, NH, NR$^9$ or N—where the remaining valence of N with Z forms a ring structure; r is 0-8, preferably 0-4, and more preferably 0, 1, or 2, Z is H or C$_{1-4}$ alkylene, preferably H or C$_{1-2}$ alkylene, the alkylene groups, when present, forming a ring structure with X when X is N—, and B is as defined previously, or is H, CH$_3$,—CH═CH$_2$, and R$^9$ is

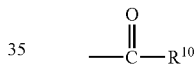

wherein R$^{10}$ is C$_{6-20}$ alkyl. Preferred compounds of this structure include those where A is substituted phenyl, X is NH, Z is H, and B is substituted phenyl, and those where X is N—, r is 0 and Z is —CH$_2$CH$_2$—, or —CH$_2$CH$_2$CH$_2$—, forming a six or seven membered ring including both nitrogens.

Examples of structural formulae encompassed by the above definition are the following where R$^2$ group shown represents one or more than one R$^2$, preferably one or two R$^2$ groups, which may occupy any ring position:

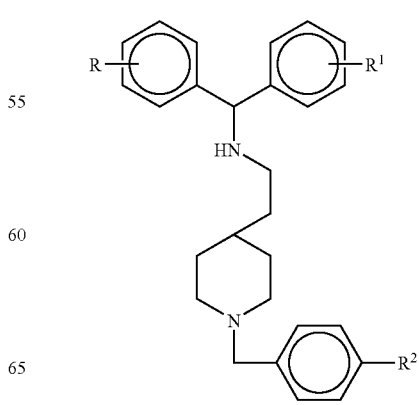

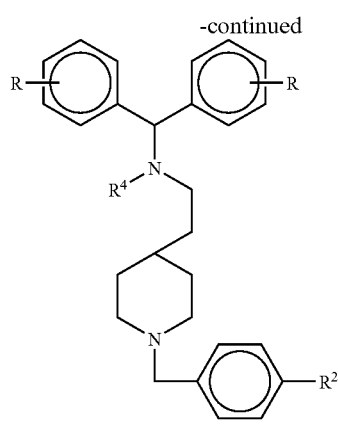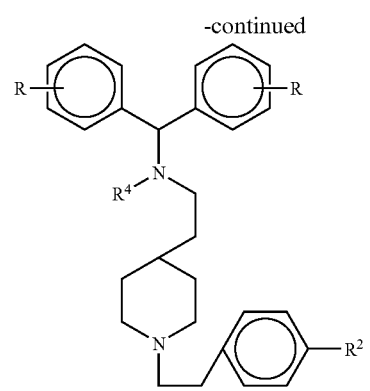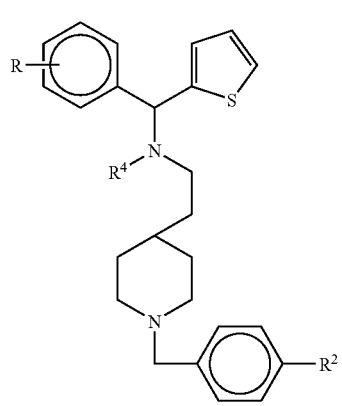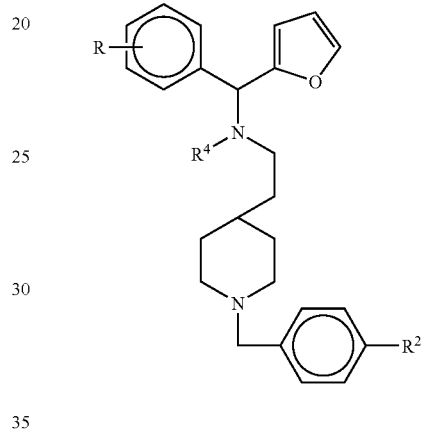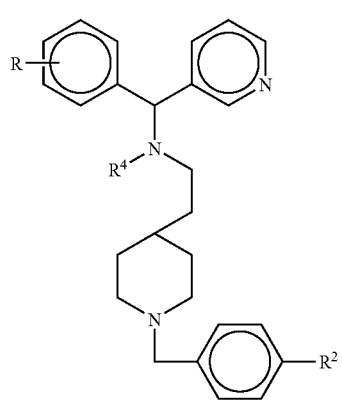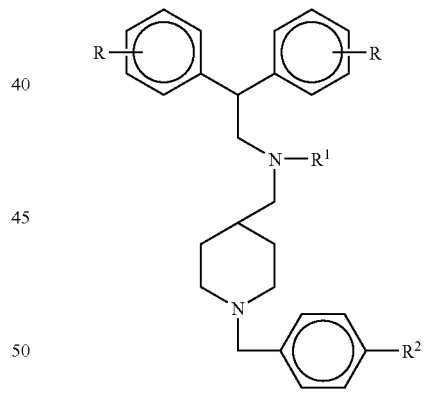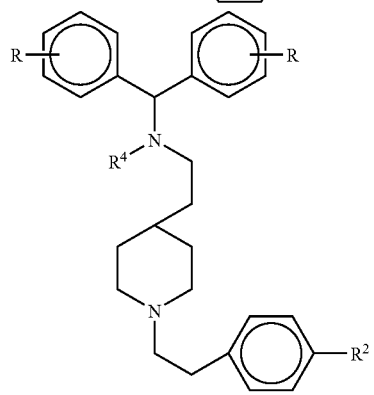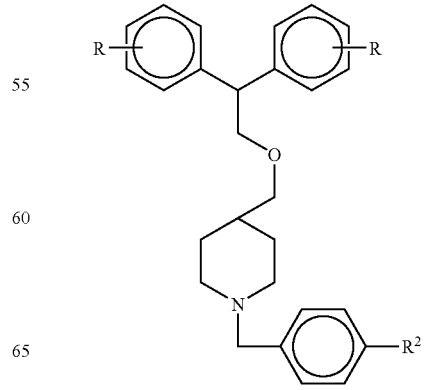

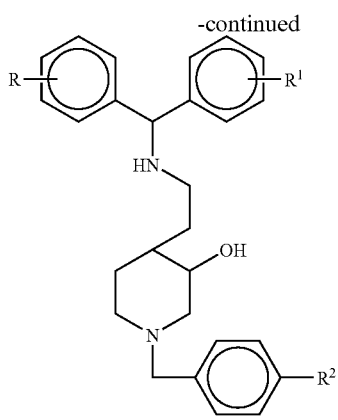
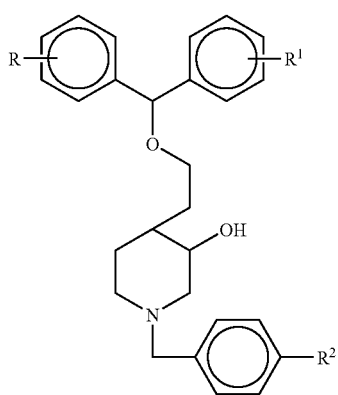
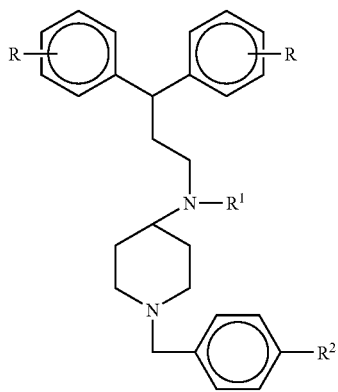
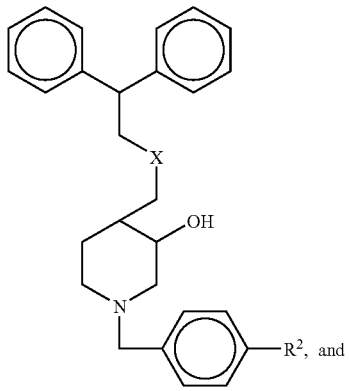
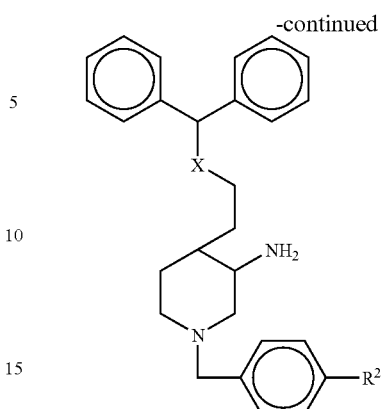
wherein in the latter two compounds, X is preferably NH or O.
Preferred compounds are those where substituents on the N-arylalkyl moiety are electronegative and electron withdrawing groups. In particular, compounds having the structural formulae
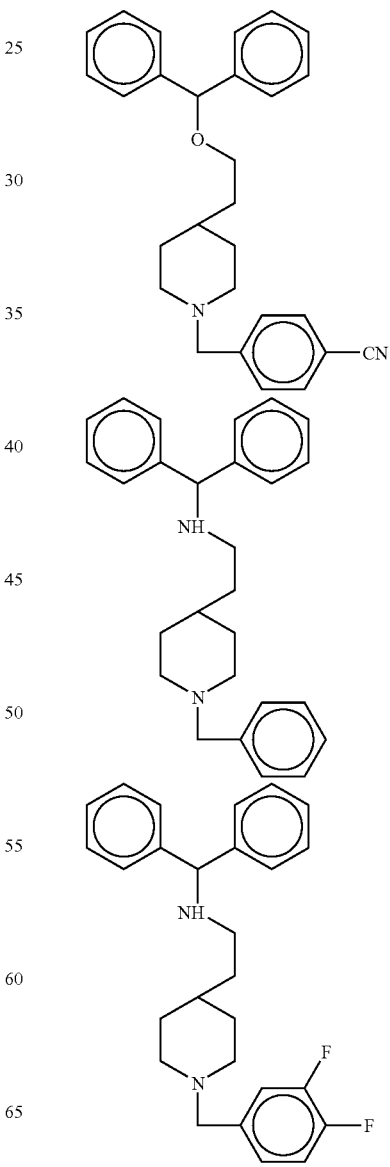

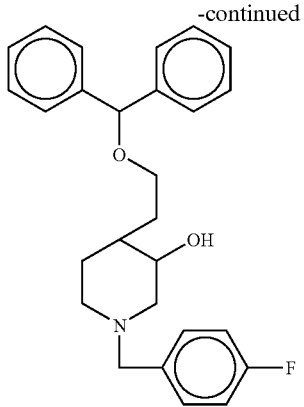

have been shown to provide unexpectedly low activity in the nanomolar range, as well as high selectivity as shown by the difference in binding affinities with respect to the DAT and SERT. In the foregoing formulae, each variant is considered as individually defined. The various replacement groups for X, and R through $R^5$ may be employed to the exclusion of any one or more than one of such replacements.

Further preferred classes of active compounds include those of structural Formula I where B is a phenyl group bearing a 4-cyano, 4-iodo, or 3,4-difluoro-group, and in particular, compounds falling within the scope of structural Formula I or its preferred subgeneric general formula, and corresponding to the following structures:

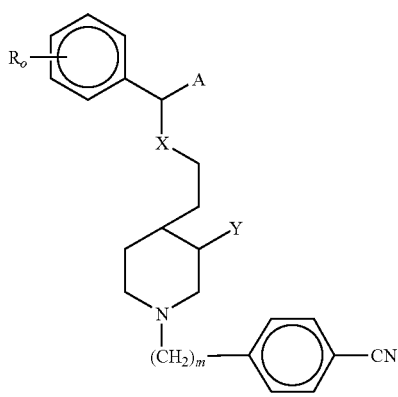

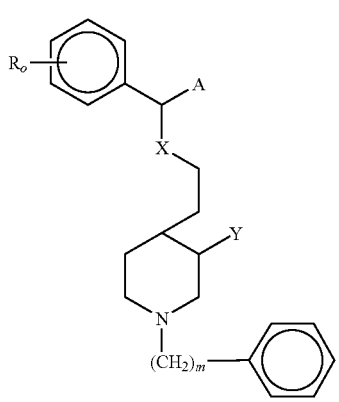

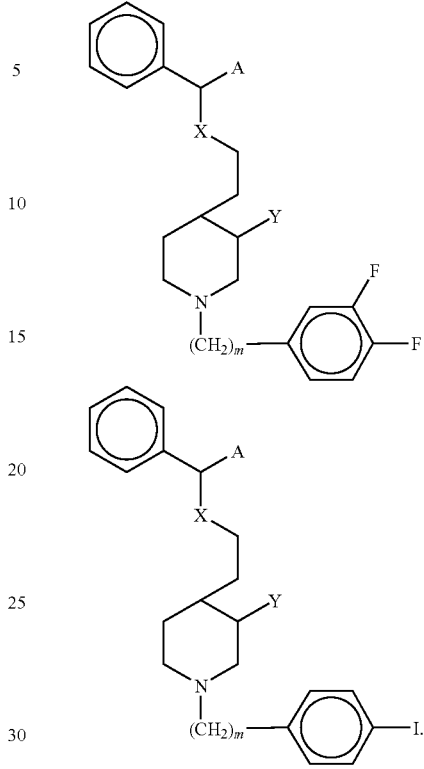

Most preferably, the active compounds of the invention correspond to compounds of the formula:

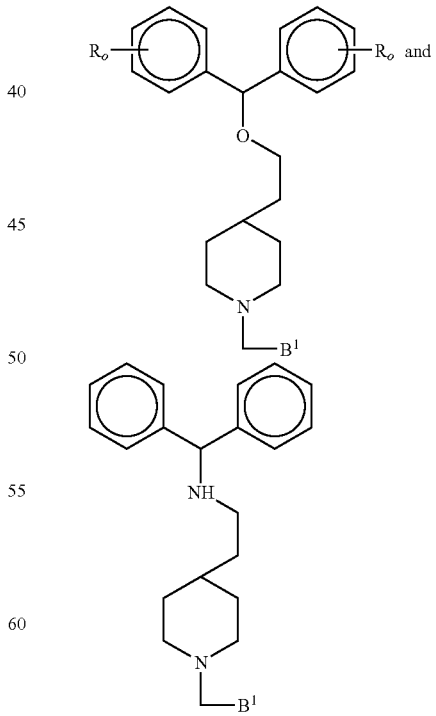

where $B^1$ is 4-cyanophenyl, 3,4-difluorophenyl, or 4-iodophenyl. In each of the more general structures above having a —$(CH_2)_m$— radical, when m is 2 or 3, any of the carbons of the —$(CH_2)_m$— moiety may be substituted by —$OR^7$ as defined above.

Further examples of preferred compounds include:

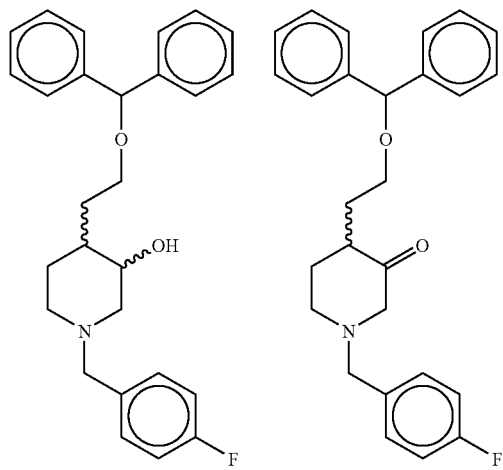

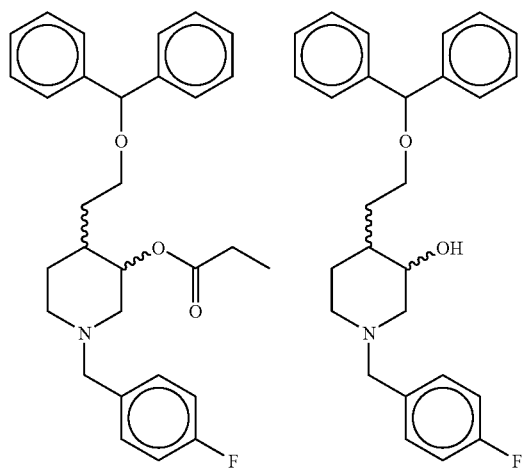

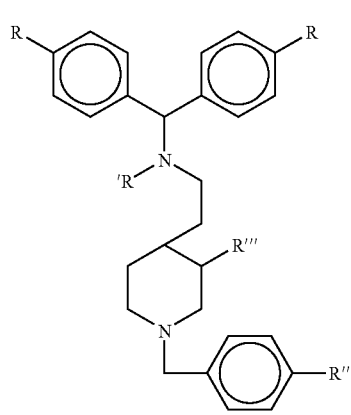

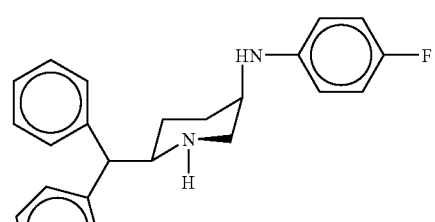

where R''' is H, OH, $NH_2$, $OR^9$, or $NHR^9$ where $R^9$ is

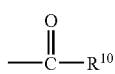

where $R^{10}$ is $C_{6-20}$ alkyl, and

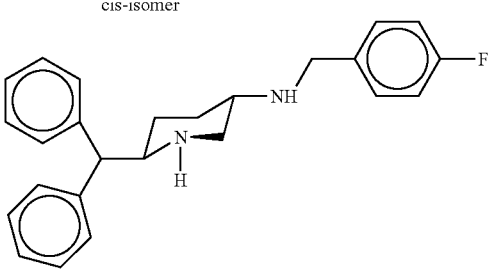

7a
cis-isomer 7b
trans-isomer

All the various geometric and stereoisomers of the subject invention compounds are useful. However, some geometric and stereoisomers have unexpectedly high activity or differential activities. One example of the latter is represented by the cis- and trans-isomers of 2-diphenylmethyl-5-(4-fluorobenzylamino)piperidine, prepared in racemic form. The cis isomer showed a selectivity ratio of 93.7 SERT/DAT, while the trans isomer showed a 6.28 selectivity ratio. Individual enantiomers are expected to exhibit yet higher activity and selectivity.

Having generally described this invention, a further understanding can be obtained by reference to certain specific examples which are provided herein for purposes of illustration only and are not intended to be limiting unless otherwise specified.

Target compounds are prepared as free bases or salts, e.g. hydrochloride, hydrobromide, oxalate, tartrate, etc. Characterization of the compounds is carried out using standard high field NMR, mass spectra, optical rotation, etc. Purity of the compounds are measured by elemental analysis, TLC or HPLC. A purity of >98% is preferred for the biological analysis of these compounds.

The rat DAT was labeled with [$^3$H]Win 35,428 and the rat SERT with [$^3$H]citalopram. Both binding assays were carried out under the same conditions with striatal tissue from male, young adult Sprague-Dawley rats, as described in M. E. A. Reith et al., "Structural Requirements for Cocaine Congeners to Interact With Dopamine and Serotonin Uptake Sites in Mouse Brain and to Induced Stereotyped Behavior", BIOCHEM. PHARMACOL., 1986, 35, 1123-1129 and A. K. Dutta et al., "Structure-Activity Relationship Studies of Novel 4-[2-[Bis(4-fluorophenyl)methoxy]ethyl]-1-(3-phenylpropyl)piperidine Analogs: Synthesis and Biological Evaluation at the Dopamine and Serotonin Transporter Sites", J. MED. CHEM., 1996, 39, 749-756. Briefly, rat striatal membranes were incubated with radioligand and inhibitor for 2 h on ice in a sodium phosphate buffer at a final Na$^+$ concentration of 30 nM, pH 7.4, at room temperature. The assays were terminated by filtration through glass fiber filtermats (Wallac, Inc., Gaithersburg, Md.), presoaked in 0.05% (v/v) polyethyleneimine, with a MACH3-96 Tomtec harvester (Wallac, Inc.). Filters were assayed for radioactivity in a Microbeta Plus liquid scintillation counter (Wallac, Inc.).

Uptake of [$^3$H]dopamine into HEK-293-hDAT cells was measured in suspended, intact cells by general techniques previously described. M. C. Ritz et al., "Cocaine Inhibition of Ligand Binding at Dopamine, Norpinephrine and Serotonin Transporters: A Structure-Activity Study", LIFE. SCI., 1990, 46, 635-645; M. J. Kaufmnan et al., SYNAPSE, 1991, 9, 43-49. Briefly, cells were preincubated with inhibitor for 15 minutes at room temperature in the same tropolone-containing buffer as described above; [$^3$H]dopamine was added and the incubation continued for another 8 minutes. Termination of the assay consisted of addition of ice-cold buffer and rapid filtration through Whatman GF/C glass fiber filters, presoaked in 0.05 % (w/v) poly-L-lysine, with a Brandel 24-pin harvester (Brandel, Inc. Gaithersburg, Md.). Radioactivity on filters was estimated by liquid scintillation counting (Beckman LS6000IC, Beckman Instruments, Inc., Fullerton, Calif.).

All compounds were dissolved in dimethylsulfoxide (DMSO) and diluted to 10% (v/v) DMSO. Additions from the latter stocks resulted in a final concentration of DMSO of 0.5%, which by itself did not interfere with radioligand binding or uptake. After initial range-finding experiments, at least five concentrations of the test compound were studied, spaced evenly around its IC$_{50}$ value. The latter was estimated by non-linear computer curve fitting procedures as described previously.

The DAT, SERT, and NET activities for these compounds make them useful in numerous ways. For example, radioligand version of these disclosed compounds will find applications as imaging agents for DAT in the CNS for SPECT and PET imaging studies. Such imaging may be used in diagnosing Parkinson's disease.

In addition, the compounds may serve as ligands for the DAT, SERT, and NET for use as comparative or base ligands when testing new candidate CNS drugs. Most importantly, however, the compounds of the subject invention, as shown by their binding affinities at low concentration, will have utility in treating CNS disorders such as drug addiction, particularly the effects of cocaine and PCP administration, and potentially the effects of administration of other psychoactive drugs, both legal and illicit. The compounds may be used to treat cocaine addiction, for example. The subject compounds also show utility, based on the in vitro studies described herein, for administration to patients suffering from Parkinson's disease and other related disorders. The compounds further have utility as antidepressants, and in treating other neurological disorders related to those above.

The studies performed to date and disclosed herein thus support the use of the presently claimed compounds in the treatment of CNS disorders in mammalian species, particularly in humans. The effective dosage will vary depending upon the particular disorder being treated. In general, the administration will be such that a concentration will be present in brain tissue and/or fluids which cause measurable binding to the DAT, SERT, or NET. This binding may be assessed by traditional techniques, including using radiolabeled compounds of the present invention or by using the compounds of the present invention to displace other radiolabeled ligands. Conventional techniques such as SPECT and PET may be used in assaying binding.

In general, the concentration of the compounds in the blood or plasma should range from about 1% of the IC$_{50}$ concentration for the respective transporter, as measured herein, to about 1000% of this concentration, more preferably from 5% to 400%, yet more preferably from 10% to 200%.

The administration may be in any pharmaceutically acceptable form, for example as a liquid containing the active compound dissolved in a suitable solvent or dispersed or emulsified in a liquid; intravenously; as a solid in tablet or capsule form; parenterally as an injected liquid, or transdermally from a transdermal patch. Each formulation may contain usual pharmaceutically acceptable additives, including but not limited to flavorants, odorants, tabletting aids, solubility enhancers, permeability enhancers, surfactants, fillers, etc. In addition, the compounds may be reacted with suitable salt formers of their pharmaceutically acceptable salts, including but not limited to acetates, formates, oxalates, tartrates, hydrochlorides, hydrobromides, hydrogen sulfates, etc.

The expected useful dosage when administered orally is from to 0.01 mg to 100 mg per kilogram of body weight, more preferably from 0.1 mg to 50 mg, yet more preferably 0.2 mg to 30 mg. Total dosage for the average adult may range from 5 mg to 500 mg, preferably 10 mg to 250 mg, and most preferably 10 mg to 150 mg. The actual dosage can be determined readily by conventional methodology.

Target compounds are prepared as free bases or salts, e.g. hydrochloride, hydrobromide or oxalate. Characterization of the compounds is carried out using standard high field NMR, mass spectra, optical rotation, etc. Purity of the compounds are measured by elemental analysis, TLC or HPLC. A purity of >98% is preferred for the biological analysis of these compounds. Several general synthetic pathways have been used herein. Other synthetic methods well known to the synthetic organic chemist may be used to prepare the compounds of the subject invention, or to derivatize these compounds.

Synthesis of Intermediates 1-(Methoxycarbonyl)-4-[(2-Diphenylmethoxy)ethyl]piperidine The solution of 4-[2-(Diphenylmethoxy)ethyl]-1-(phenylmethyl)piperidine (4.62 g, 11.82 mmol) and methyl chloroformate (2.60 g, 23.53 mmol) in bezene (60 ml) was refluxed for 6 hours. After T.L.C. showed the completion of reaction, the solvent was removed under vacuo to give a viscous liquid 1-(methoxycarbonyl)-4-[(2-diphenylmethoxy)ethyl]piperidine, 4.17 g (99% yield). $^1$H NMR (CD$_3$Cl) δ 7.34-7.18 (10H, m, Ar—H), 5.30 (1H, s, Ph$_2$CHO), 3.67 (3H, s, OCH$_3$), 3.50-3.46 (2H, t, J=6.0Hz, OCH$_2$), 2.77-2.68 (2H, t, J=12.3Hz, N(CH)$_2$), 2.62-2.54 (2H, t, J-12.0 Hz, N(CH)$_2$), 1.67-1.57 (5H, m), 1.26-1.07 (2H, m).

4-[(2-Diphenylmethoxy)ethyl]piperidine 1-(methoxycarbonyl)-4-[(2-diphenylmethoxy)ethyl]piperidine (4.17 g, 11.81 mmol) was dissolved in ethanol (100 ml), KOH (2.5 g) was added into the solution. The reaction solution was refluxed for 3 days. The solvent was evaporated and EtOAc was added. The EtOAc solution was washed by brine, dried over Na$_2$SO$_4$, and evaporated to give a crude product, which was purified by chromatography (EtOAc/MeOH/Et$_3$N=100/5/2) to give a white solid 4-[(2-diphenylmethoxy)ethyl]piperidine, 2.80 g (80% yield). $^1$H NMR (CD$_3$Cl) δ 7.35-7.19 (10H, m, Ar—H), 5.31 (1H, s, Ph$_2$CHO), 3.50-3,46 (2H, t, J=6.0 Hz, OCH$_2$), 3.08-3.04 (2H, bd, J=2.3 Hz, N(CH)$_2$), 2.77-2.68 (2H, t, J=12.6 Hz), 2.62-2.54 (2H, t, J=12.3 Hz, N(CH)$_2$), 1.82-1.57 (5H, m), 1.14-1.02 (2H, m). Anal. [C$_{20}$H$_{25}$NO·2.0H$_2$O] Calculated: C, 79.90; H, 8.58; N, 4.66; Found: C, 79.86; H, 8.59; N, 4.70.

N-Benzhydryloxyphthalimide

A solution of 1-chloro-1, 1-diphenylmethane (3.42 g, 16.93 mmol), N-hydroxyphthalimide (2.30 g, 14.11 mmol) and Et$_3$N (3.0 ml) in DMF (50 ml) was stirred at 60° C. under N$_2$ for 8 hours. After the reaction mixture was cooled to room temperature, water (100 ml) was added. The mixture was extracted with Et$_2$O. The combined organic phase was dried over Na$_2$SO$_4$. After evaporation of the solvent, the crude product was purified by chromatography(Hexane/Benzene/EtOAc=20/10/3) to give a white solid, 3.95 g (85% yield). $^1$H NMR (CD$_3$Cl) δ 7.72-7.63 (1H, m), 7.56-7.53 (1H, m), 7.40-7.24 (12H, m), 5.85 (1H, s, Ph$_2$CH).

O-Benzyhydrylhydroxylamine

N-Benzhydryloxyphthalimide (1.03 g, 3.14 mmol) was dissolved in EtOH (20 ml). NH$_2$NH$_2$ (0.3 ml) was added into the EtOH solution. After the reaction mixture was stirred at room temperature for 0.5 h., EtOH was removed under vacuo and EtOAc (60 ml) was added. The mixture was filtered. The solution was collected and dried over Na$_2$SO$_4$. After the evaporation of solvent, the crude product was purified by chromatography(Hexane/EtOAc=5/1) to give a viscous oil 0.31 g (50% yield). $^1$H NMR (CD$_3$Cl) δ 7.34-7.26 (10H, m, AR-H), 5.65 (1H, s, Ph$_2$CH).

1-[(4-Fluorophenyl)methyl]-4-piperidinemethanol

Dry THF (50 ml) was added dropwise into lithium aluminum hydride (0.7 g) under N$_2$ in ice bath. 1-[(4-Fluorophenyl)methyl]-4-(ethoxycarbonyl) piperidine (1.21 g, 4.57 mmol) in dry THF (10 ml) was added dropwise into the LAH suspension solution. The reaction mixture was refluxed for 2 hours. Saturated NaOH/H$_2$O (3 ml) was added dropwise and the reaction cooled by an ice bath. The mixture was filtered. The solution was dried over Na$_2$SO$_4$ and evaporated to produce 11 0.98 g (98% yield). $^1$H NMR (CD$_3$Cl) δ 7.36-7.26 (2H, m, Ar—H), 7.07-6.96 (2H, m, Ar—H), 4.66 (1H, s, OH), 3.50-3.48 (2H, d, J=6.0 Hz, CH20H), 3.46 (2H, s, F-PhCH$_2$), 2.90-2.87 (2H, bd, J=11.1 Hz, N(CH)$_2$), 1.99-1.91 (2H, dt, J=1.8, 11.8 Hz, N(CH)$_2$), 1.73-1.68 (3H, m), 1.34-1.22 (2H, m).

1-[(4-Fluorophenyl)methyl]-4-piperidinecarboxaldehyde

A solution of oxylyl chloride (0.59 ml, 3.95 mmol) in CH$_2$Cl$_2$ (20 ml) was cooled to –78° C. DMSO (0.95 ml, 13.38 mmol) was added dropwise into the oxylyl chloride solution. The reaction mixture was stirred for 5 minutes, and 1-[(4-fluorophenyl)methyl]-4-piperidinemethanol (0.99 g, 4.46 mmol) in CH$_2$Cl$_2$ (20 ml) was added dropwise into the reaction solution. Stirring was continued for an additional 20 minutes. Et$_3$N, 8.0 ml was added and the reaction mixture was stirred for 10 minutes and then allowed to warm to room temperature. Water (50 ml) was added and the mixture was extracted with CH$_2$Cl$_2$. The combined CH$_2$Cl$_2$ solution was dried over Na$_2$SO$_4$. The evaporation of solvent gave an oil, 0.77 g (79% yield). $^1$H NMR (CD$_3$Cl) δ 9.65 (1H, s, CHO), 7.30-7.24 (2H, m, Ar—H), 7.00-6.97 (2H, m, Ar—H), 3.46 (2H, s, p-FPhCH$_2$), 2.81-2.76 (2H, m, N(CH)$_2$), 2.30-2.20 (1H, m, CHCHO), 2.14-2.06 (2H, dt, J=2.1, 11.3 Hz, N(CH)$_2$), 1.92-1.86 (2H, dd, J=3.5, 13.5 Hz), 1.74-1.62 (2H, m).

4-[(2-Diphenylethyl)aminocarbonyl]-1-[(4-fluorophenyl)methyl]piperidine

1-[(4-Fluorophenyl)methyl]-4-(ethoxycarbonyl)piperidine (0.68 g, 2.72 mmol) was converted into its carboxylic acid, which was then reacted with 2,2-diphenylethyl amine (0.67 g, 3.40 mmol), EDCI (0.76 g, 3.95 mmol), and HOBT (0.62 g, 4.59 mmol) to produce 4-[(2-diphenylethyl)aminocarbonyl]-1-[(4-fluorophenyl)methyl]piperidine, 0.84 g (75% yield)(procedure D). $^1$H NMR (CD$_3$Cl) δ 7.36-7.20 (12H, m, Ar—H), 7.01-6.95 (2H, m, Ar—H), 5.39 (1H, bs, NH), 4.21-4.15 (1H, t, J=7.8 Hz, Ph$_2$CH), 3.91-3.86 (2H, t, J=7.5 Hz, CH$_2$NH), 3.41 (2H, s, p-FPhCH$_2$), 2.84-2.80 (2H, d, J=11.4 Hz, N(CH)$_2$), 1.96-1.87 (3H, m, NHCOCH, NH(CH)$_2$), 1.65-1.58 (4H, m).

4-[(Bis(4-fluorophenyl)ethylamino)carbonyl-1-(phenylethyl)piperidine 1-(phenylethyl)-4-(ethoxycarbonyl)piperidine (0.25 g, 0.95 mmol) was converted into its carboxylic acid, which was then reacted with bis(4-fluorophenyl)methyl amine (0.25 g, 1.14 mmol), EDCI (0.25 g, 1.27 mmol), HOBT (0.20 g, 1.48 mmol) in Et$_3$N (1.5 ml) and CH$_2$Cl$_2$ (20 ml) to produce 4-[(bis(4-fluorophenyl)ethylamino)carbonyl-1-(phenylethyl)piperidine, 0.32 g (74% yield)(procedure E). $^1$H NMR (CD$_3$Cl) δ 7.29-7.03 (10H, m, Ar—H), 7.05-6.99 (3H, m, Ar—H), 6.22-6.20 (1H, d, J=7.8 Hz), p-FPh$_2$CH), 6.00-5.97 (1H, d, J=7.5 Hz, NH), 3.08-3.04 (2H, bd, J=11.4 Hz, N(CH)$_2$), 2.83-2.78 (2H, d), 2.62-2.57 (2H, m), 2.25-2.15 (1H, m, NCOCH), 2.10-2.03 (2H, t, J=11.4 Hz, N(CH)$_2$), 1.96-1.81 (4H, m).

4-[(1-Phenylethyl)aminocarbonyl]methyl-1-[(4-fluorophenyl)methyl]piperidine

1-[(4-fluorophenyl)methyl]-4-[(ethoxycarbonyl)methyl] piperidine (0.55 g, 1.97 mmol) was refluxed in CF$_3$CO$_2$H/HCl/H$_2$O (1:1:1) 10 ml to give the corresponding acid, which was then reacted with 1-phenylethylamine (0.29 g, 2.40 mmol), EDCI (0.56 g, 2.97 mmol) and HOBT (0.40 g, 2.96 mmol) in CH$_2$Cl$_2$ (10 ml) to produce a solid, 0.33 g (50% yield)(procedure D). $^1$H NMR (CD$_3$Cl) δ 7.35-7.23 (7H, m, Ar—H), 7.00-6.94 (2H, t, J=8.4 Hz, Ar—H), 5.83-5.80 (1H, bd, J=7.5 Hz, NH), 5.15-5.10 (m, 1H, PhCHMe), 3.42 (s, 2H, p-PhCH$_2$N), 2.83-2.78 (m, 2H, N(CH)$_2$), 2.07-2.05 (2H, d, J=7.2 Hz, CH$_2$CO), 1.99-1.89 (2H, m), 1.86-1.78 (1H, m), 1.71-1.61 (2H, t, J=15 Hz), 1.48-1.45 (3H, d, J=6.9 Hz, Me), 1.33-1.21 (2H, m).

Synthesis of 2-(Diphenylcyanomethyl)-5-nitropyridine

To a mixture of 1.0 g 2-chloro-5-nitropyridine (6.3 mmol), 1.33 g diphenylacetonitrile (6.9 mmol, 1.1 equiv) and 700 mg tetrabutylammonium fluoride (3.15 mmol, 0.5 equiv) in 3 mL toluene was added dropwise 1.5 mL 50% aqueous NaOH. After 30 min, no starting materials remained by TLC (hexane/EtOAc). The mixture was filtered through a short plug of silica to remove tars, evaporated and chromatographed (SiO$_2$; hexane/EtOAc). The crude product was a slightly yellow oil which was recrystallized from MeOH to furnish the title compound (1.7 g, 86%) as colorless plates. mp 94-9° C. $^1$H NMR (CDCl$_3$; 300 MHz) 7.20-7.29 (5H, m), 7.35-7.42 (5H, m), 7.54 (1H, d, J=8.7 Hz, H-3), 8.49 (1H, dd, J=3 and 9 Hz, H-4), 9.60 (1H, d, J=2.4 Hz, H-6). $^{13}$C NMR (CDCl$_3$; 300 MHz) 60.19, 121.65, 123.77, 128.87, 129.09, 129.33, 132.52, 138.46, 143.49, 145.31, 164.99. Elemental analysis calculated for $C_{19}H_{13}N_3O_2$: C, 72.38; H, 4.13; N, 13.33. Found: C, 72.35; H, 4.08; N, 13.25.

Synthesis of 2-(Diphenylacetamidomethyl)-5-nitropyridine

A mixture of 5.0 g 2-(diphenylcyanomethyl)-5-nitropyridine (15.8 mmol) was added to a magnetically-stirred, room temperature solution of 40 mL conc. H$_2$SO$_4$ diluted with 10 mL H$_2$O. The mixture was then heated to 90° C., until all starting material consumed by TLC (~2 hr). The dark solution was then poured onto crushed ice and water and stirred for 1 hr, the crude title compound precipitates. The mixture was extracted thrice with EtOAc and these were pooled, dried (MgSO$_4$, with filtration through short plug of Celite) and evaporated. Dry-column chromatography (silica; hexane/EtOAc/MeOH) furnished the title compound (4.74 g, 90%) as a amorphous tan solid. mp 160-4° C. $^1$H NMR (CDCl$_3$; 300 MHz) 5.9 (1H, bs, NH), 7.05-7.1 (4H, m, ArH), 7.26 (1H, d, J=2.4 and 6.3 Hz, H4), 9.43 (1H, d, J=1.8 Hz, H-6). $^{13}$C NMR (CDCl$_3$; 400 MHz) 126.78, 128.02, 128.64, 130.25, 131.68, 142.09, 143.43, 169.44, 173.99. Elemental analysis calculated for $C_{19}H_{15}N_3O_3$; C, 68.47; H, 4.50; N, 12.61. Found: C, 68.49; H, 4.55; N, 12.60.

Synthesis of Diphenyl-(5-amino-2-pyridyl)acetamide

A mixture of 8.86 g of diphenyl-(5-nitro-2-pyridyl)acetamide (26.5 mmol) in 50% EtOH/glacial AcOH with 100 mg platinum (IV) oxide was shaken on a Parr hydrogenator (30 psi H$_2$) for 3 hr. The mixture was filtered through a bed of Celite, then the ethanol was evaporated under reduced pressure. The mixture was then basified with K$_2$CO$_3$ and extracted with EtOAc (4x), dried (MgSO$_4$), filtered through Celite again and evaporated. The remaining solid was recrystallized from hexane/EtOAc/MeOH to furnish the title compound (7.9 g, 98%) as a tan crystal. mp 215-20° C. $^1$H NMR (CDCl$_3$; 300 MHz) δ 3.85 (2H, bs, NH), 5.88 (1H, bs, CONH), 6.54 (1H, d, J=8.4 Hz), 6.84 (1H, dd, J=3 and 8.7 Hz), 7.01 - 7.06 (4H, m), 7.24-7.32 (6H, m), 8.11 (1H, d, J=2.4 Hz, H-6), 9.57 (1H, bs, CONH). Elemental analysis calculated for $C_{19}H_{17}N_3O$  0.25 H$_2$O: C, 74.15; H, 5.69; N, 13.67. Found: C, 74.06; N, 5.69; H, 13.78.

Synthesis of 2-Diphenylmethyl-5-aminopyridine

A mixture of 5.28 g diphenylmethyl-(5-amino-2-pyridyl)acetamide (17.4 mmol) and 150 mL 37% HCl under a N$_2$ atmosphere was refluxed until all starting material was consumed by TLC (~18 hr). The mixture was then cooled and poured into 300 g ice and H$_2$O and basified with K$_2$CO$_3$. The mixture was extracted thrice with EtOAc (150 mL), dried (MgSO$_4$) and evaporated to a green oil that solidified. This was chromatographed (SiO$_2$; hexane/EtOAc) to furnish the title compound (4.09 g, 90%) as a tan crystalline solid. mp 130-4° C. $^1$H NMR (CDCl$_3$; 300 MHz) δ 3.52 (2H, bs, NH), 5.61 (1H, s, CH(C$_6$H$_5$)$_2$), 6.83-6.91 (2H, m, ArH), 7.15-7.32 (10H, m, ArH), 8.08 (1H, d, J=2.4 Hz, H-6). $^{13}$C NMR (CDCl$_3$; 300 MHz) 58.61, 122.38, 123.98, 126.55, 128.57, 129.56, 137.31, 140.77, 143.64, 153.39. Elemental analysis calculated for $C_{18}H_{16}N_2$; C, 83.08; H, 6.15; N, 10.77. Found: C, 82.82; H, 6.30; N, 10.81.

Synthesis of racemic cis- and trans-2-Diphenylmethyl-5-aminopiperidine

To a solution of 454 mg 2-diphenylmethyl-5-aminopyridine dihydrochloride salt (3.83 mmol) and 20 mL MeOH was added 50 mg platinum (IV) oxide and the mixture was shaken at room temperature under a H$_2$ atmosphere (60 psi) for 10 hr. The mixture was then filtered through Celite and the MeOH was evaporated. The remaining residue was diluted with saturated K$_2$CO$_3$ and extracted with CH$_2$Cl$_2$ (5x). The extracts were pooled, dried (MgSO$_4$) and evaporated to a colorless oil. The oil was chromatographed (SiO$_2$; CH$_2$Cl$_2$/MeOH/triethylamine) to furnish 300 mg (82%) of the title compounds as a colorless oil. The oil solidified upon addition of EtO$_2$. A sample of this mixture of diastereomers was separated by PTLC (SiO$_2$; hexanes/EtOAc/MeOH). Eluting first: racemic cis-2diphenylmethyl-5-aminopiperidine, $^1$H NMR (CDCl$_3$; 400 MHz) δ 1.35-1.45 (2H, m, H-3), 1.55 -1.65 (2H, m, H4), 2.08 (3H, bs, NH), 2.77-2.82 (2H, s, H-6) 3.0 (1H, m, $\Sigma^3$J=13 Hz, H-5eq), 3.25 (1H, dt, $^3$J=4.0 and 8.8 Hz, H-2ax), 3.81 (1H, d, $^3$J=10.4 Hz, CH(C$_6$H$_5$)$_2$), 7.1-7.4 (10H, m, ArH). Eluting second: racemic trans-2-diphenylmethyl-5-aminopiperidine, $^1$H NMR (CDCl$_3$; 400 MHz) δ 1.1-1.25 (2H, m, H-3ax, H4ax), 1.55-1.6 (1H, m, H-3eq), 1.9-1.96 (1H, m, H4eq), 2.13 (3H, bs, NH), 2.35 (1H, t, $^2$J and $^3$J=10.8 Hz, H-6ax), 2.85 (1H, m, $\Sigma^3$J=38 Hz, H-5ax), 3.11 (1H, d, $^2$J=9.2 Hz, H-6eq), 3.19 (1H, t, $^3$J=10.8 Hz, H-2ax), 3.69 (1H, d, $^3$J=10 Hz, CH(C$_6$H$_5$)$_2$), 7.15-7.4 (10H, m, ArH). The $^1$H NMR (CDCl$_3$; 400 MHz) of the purified, unseparated mixture of the title compounds showed the ratio of 60 cis: 40 trans based on integration (CH(C$_6$H$_5$)D.

EXAMPLES

Example 1

4-[2(Diphenylmethoxy)ethyl]-1-[(3-fluorophenyl)methyl]piperidine

A mixture of 4-[(2-Diphenylmethoxy)ethyl]piperidine 4 (58 mg, 0.19 mmol), 3-fluorobenzyl chloride (51 mg, 0.35 mmol), Et$_3$N (0.5 ml), and anhydrous K$_2$CO$_3$ (0.3 g) in DMF (10 ml) was stirred at 65° C. overnight. The reaction mixture was diluted with 30 ml water and extracted with Et$_2$O. The combined organic phase was dried over Na$_2$SO$_4$ and evaporated to give a crude product, which was purified by chromatography (EtOAc/Hexane=1/3) to give 4-[2-(diphenylmethoxyethyl]-1-[(3-fluorophenyl)methyl]piperidine, a viscous liquid 62 mg (79% yield) ("Procedure A"). $^1$H NMR (CD$_3$Cl) δ 7.34-7.20 (10H, m, 2Ph), 7.11-7.03 (3H, m, m-FPh), 6.95 (1H, m, m-FPh), 5.31 (1H, s, Ph$_2$CH), 3.45-3.44 (2H, t, L=6.6 Hz, OCH$_2$), 3.44 (2H, s, m-FPhCH$_2$), 2.84-2.80 (2H, bd, J=11.1 Hz, N(CH)$_2$), 1.97-1.89 (2H, t, J=11.4 Hz, N(CH)$_2$), 1.63-1.51 (4H, m), 1.49-1.44 (1H, m), 1.29-1.21 (2H, m). The free base was converted into its oxalate salt, m.p.=150-151° C. Anal. [C$_{27}$H$_{30}$NOF·(COOH)$_2$·0.3H$_2$O] Calculated: C, 69.79; H, 6.58; N, 2.80; Found: C, 69.87; H, 6.80, N, 2.76.

Example 2

4-[2-(Diphenylmethoxy)ethyl]-1-[(3,4-difluorophenyl)methyl]piperidine

4-[(2-Diphenylmethoxy)ethyl]piperidine 4 (0.12 g, 0.42 mmol) was reacted with (3,4difluoro)benzyl bromode (0.17 g, 0.82 mmol), Et$_3$N (0.5 ml), and K$_2$CO$_3$ (0.6 g) in dry DMF (10 ml) to give 4-[2-(diphenylmethoxy)ethyl]-1-[(3,4-difluorophenyl)methyl]piperidine, 0.15 g (86% yield), as a viscous liquid (procedure A). $^1$H NMR (CD$_3$Cl) δ 7.34-6.99 (13H, m, Ar—H), 5.31 (1H, s, Ph$_2$CH), 3.49-3.45 (2H, t, J=6.3 Hz, OCH$_2$), 3.85 (s, 2H, NCH$_2$Ph), 2.80-2.77 (2H, d, J=11.4 Hz, N(CH$_2$)$_2$), 1.95-1.87 (2H, t, J=11.4 Hz, N(CH$_2$)$_2$), 1.63-1.55 (4H, m), 1.50-1.42 (1H, m), 1.28-1.15 (2H, m). The free base was converted into its oxalate salt, m.p.=158-159° C. Anal. [C$_{27}$H$_{29}$NOF$_2$·(COOH)$_2$] Calculated: C, 68.07; H, 6.11; N, 2.73; Found: C, 68.18; H, 6.13, N, 2.73.

Example 3

4-[2(Diphenylmethoxy)ethyl]-1-[((4-trifluoromethyl)phenyl)methyl]piperidine

4-[(2-Diphenylmethoxy)ethyl]piperidine 4 (0.11 g, 0.37 mmol) was reacted with (4-trifluoromethyl)benzyl chloride (0.14 g, 0.72 mmol), Et$_3$N (0.5 ml) and K$_2$CO$_3$ (0.5 g) in DMF (10 ml) to give 4-[(diphenylmethoxy)ethyl]-1-[((4-trifluoromethyl)phenyl)methyl]piperidine, 0.15 g (92% yield), as a viscous liquid (procedure A). $^1$H NMR (CD$_3$Cl) δ 7.64-7.47 (4H, m, CF$_3$Ph), 7.34-7.23 (10H, m, 2Ph), 5.31 (s, Ph$_2$CH), 3.52 (2H, s, p-FPhCH$_2$), 3.49-3.45 (2H, t, J=6.3 Hz, OCH$_2$), 2.84-2.80 (2H, d, J=11.1 Hz, N(CH$_2$)$_2$), 2.00-1.92 (2H, t, J=11.1 Hz, N(CH$_2$)$_2$), 1.63-1.55 (4H, m), 1.49-1.42 (1H, m), 1.27-1.15 (2H, m). The free base was converted into its oxalate salt, m.p.=149-150° C. Anal. [C$_{27}$H$_{30}$NOF$_3$·(COOH)$_2$·0.70H$_2$O] Calculated: C, 64.77; H, 6.05; N, 2.51; Found: C, 65.15; H, 6.46, N, 2.40.

Example 4

4-[2-(Diphenylmethoxy)ethyl]-1-[(4-cyanophenyl)methyl]piperidine

4-[(2-Diphenylmethoxy)ethyl]piperidine 4 (0.15 g, 0.52 mmol) was reacted with 4-cyanobenzyl bromide (0.18 g, 0.92 mmol), Et$_3$N (0.5 ml) and K$_2$CO$_3$ (0.7 g) in DMF 10 ml to give 4-[2-(diphenylmethoxy)ethyl-1-[(4-cyanophenyl)methyl]piperidine, 0.17 g (84% yield), as a white solid (procedure A). $^1$H NMR (CD$_3$Cl) δ 7.61-7.58 (2H, d, J=7.5 Hz, Ar—H), 7.45-7.42 (2H, d, J=7.5 Hz, Ar—H), 7.33-7.22 (10H, m, Ar—H), 5.31 (1H, s, Ph$_2$CHO), 351 (2H, s, p-CN-PhCH$_2$), 3.50-3.46 (2H, t, J=6.0 Hz, OCH$_2$CH$_2$), 2.81-2.77 (2H, bd, J=10.8 Hz, N(CH$_2$)$_2$), 2.00-1.93 (2H, t, J=11.1 Hz, N(CH$_2$)$_2$), 1.65-1.56 (4H, m), 1.52-1.46 (1H, m, OCH$_2$CH$_2$CH), 1.30-1.18 (2H, m). The free base was converted into its oxalate salt, m.p.=120-121° C. Anal. [C$_{28}$H$_{30}$N$_2$O)·(CO$_2$H)$_2$·0.26H$_2$O] Calculated: C, 71.32; H, 6.48; N, 5.54; Found: C, 71.32; H, 6.69; N, 5.39.

Example 5

4-[2-(Diphenylmethoxy)ethyl]-1-[(phenylethyl)carbonyl]piperidine

A solution of phenylacetic acid (0.11 g, 0.82 mmol), 1-[3-(dimethylamino)propyl]-3-ethylcarbodiimidehydrochloride (EDCI) (0.17 g, 0.88 mmol), and 1-hydroxybenzotriazole (OBT) (0.11 g, 0.88 mmol) in Et$_3$N (1 ml) and dry CH$_2$Cl$_2$ (10 ml) was stirred at room temperature for 1 hour. 4-[(2-diphenylmethoxy)ethyl] piperidine 4 (0.12 g, 0.41 mmol) in CH$_2$Cl$_2$ (5 ml) was added. The solution was stirred at room temperature overnight. The solvent was removed in vacuo, the residue was dissolved in EtOAc. The organic phase was washed with 5% citric acid aqueous solution, followed by saturated NaHCO$_3$ solution, and dried over Na$_2$SO$_4$. The organic extract was evaporated to give a crude product, which was purified by chromatography (EtOAc/Hexane=1/3) to collect a viscous liquid 4-[2-(diphenylmethoxy)ethyl]-1-[(phenylmethyl)carbonyl]piperidine(5e), 0.27 g (96% yield) ("Procedure B"). $^1$H NMR (CD$_3$Cl) δ 7.32-7.25 (15H, m, Ar—H), 5.29 (1H, s, Ph$_2$CHO), 4.62-4.58 (1H, d, J=12.6 Hz, NCH), 3.84-3.79 (1H, d, J=13.2 Hz, NCH), 3.72 (2H, s, PhCH$_2$), 3.47-3.43 (2H, t, J=6.2 Hz, OCH$_2$), 2.96-2.88 (1H, t, J=12.6 Hz, NCH), 2.58-2.50 (1H, t, J=12.3 Hz, NCH), 1.68-1.52 (3H, m), 1.27-1.19 (2H, m), 1.10-1.03 (1H, m), 0.89-0.081 (1H, m). Anal. [C$_{28}$H$_{31}$O$_2$N·0.12H$_2$O] Calculated: C, 80.90; H, 7.51; N, 3.37; Found: C, 80.87; H, 7.50; N, 3.27.

EXAMPLE 6

4-[2-(Diphenylmethoxy)ethyl]-1-[((4-methylsulfonylamino)phenyl)methyl]piperidine 4-[(2-Diphenylmethoxy)ethyl]-1-[((4-amino)phenyl)methyl]piperidine (0.11 g, 0.29 mmol) was dissolved in CH$_2$Cl$_2$ (5 ml). CH$_3$SO$_2$Cl (0.04 g) and Et$_3$N (0.1 ml) were added. The reaction mixture was stirred at room temperature overnight. The solvent was evaporated and EtOAc 60 ml was added. The organic phase was washed by saturated NaHCO$_3$/H$_2$O and brine, and dried over Na$_2$SO$_4$. After evaporation, the crude product was purified by chromatography (EtOAc/MeOH=100/1) to give the pure compound 4-[(2-diphenylmethoxy)ethyl]-1-[((4-methylsulfonylamino)phenyl)methyl]piperidine 26 mg (20% yield) $^1$H NMR (CD$_3$Cl) δ 7.41-7.14 (14H, m, Ar—H), 5.31 (1H, s, Ph$_2$CHO), 3.49-3.34 (4H, m, OCH$_2$CH$_2$, NCH$_2$Ph), 3.40 (1H, 5, NH), 2.98 (3H, s, CH$_3$SO$_2$), 2.85-2.81 (2H, bd, J=10.8 Hz, N(CH$_2$)$_2$), 1.97-1.90 (2H, t, J=10.8 Hz, N(CH$_2$)$_2$), 1.64-1.51 (4H, m), 1.50-1.45 (1H, m, O(CH$_2$)$_2$CH, 1.28-1.17 (2H, m). The free base was converted into its oxalate salt, m.p.=122-124° C. Anal. [C$_{28}$H$_{34}$N$_2$O$_3$S·(COOH)·1.15H$_2$O] Calculated: C, 61.14; H, 6.55; N, 4.75; Found: C, 61.14; H, 6.42; N, 4.71.

EXAMPLE 7

4-[((2-Diphenylmethoxy)amino)methyl]-1-[(4-fluorophenyl)methyl]piperidine

To a solution of O-Benzyhydrylhydroxylamine 9 (0.25 g, 1.27 mmol) and aldehyde 1-[(4-fluorophenyl)methyl]-4-piperidinecarboxaldehyde (0.28 g, 1.27 mmol) in ClCH$_2$CH$_2$Cl (20 ml) was added Na(OAc)$_3$BH (0.54 g, 2.55 mmol). The reaction mixture was stirred at room temperature overnight. EtOAc 80 ml was added and the solution was washed by saturated NaHCO$_3$/H$_2$O and brine. The organic phase was dried over Na$_2$SO$_4$ and evaporated to give crude product, which was purified by chromatography (EtOAc/Hexane=1/2) to give a colorless oil, 0.43 g (84% yield). $^1$H NMR (CD$_3$Cl) δ 7.36-7.23 (12H, m, Ar—H), 7.01-6.95 (2H, t, J=7.4 Hz, Ar—H), 3.41 (2H, s, p-F-PhCH$_2$), 2.82-2.78 (2H, bd, J=11.1 Hz, N(CH$_2$)$_2$), 2.25-2.21 (1H, m, NH), 2.00-1.93 (2H, t, J=10.8 Hz, N(CH$_2$)$_2$), 1.71-1.47 (7H, m). The free base was converted into its oxalate salt, m.p.=154-155° C. Anal. [C$_{26}$H$_{29}$FN$_2$O·(COOH)·0.10H$_2$O] Cacl C, 67.88, H, 6.32; N, 5.65; Found: C, 67.62; H, 5.90; N, 5.51.

EXAMPLE 8

4-[2-((Diphenylmethyl)amino)ethyl]-1-[(3,4-difluorophenyl)methyl]piperidine

To the solution of 4-[2-diphenylmethyl)aminocarbonyl]methyl-1-[(3,4-difluorophenyl)methyl]piperidine (0.12 g, 0.28 mmol) in dry THF 20 ml was added 1M BH$_3$/THF (1.0 ml). The reaction solution was refluxed for 6 hours. After the solution was cooled to room temperature, MeOH (5 ml) was added slowly. The solvent was removed under reduced pressure. 10% HCl/MeOH (10 ml) was added into the residue and the solution was refluxed for 1 hour. Solid NaHCO$_3$ was added after MeOH was evaporated. The mixture was extracted with EtOAc. The combined organic phase was dried over Na$_2$SO$_4$ and evaporated to give the crude product, which was purified by chromatography (Hexane/EtOAc/Et$_3$N=1/2/1%) to a white solid, 0.11 g (90% yield) ("Procedure E"). $^1$H NMR (CD$_3$Cl) δ 7.39-6.99 (13H, m, Ar—H), 4.79 (1H, s, Ph$_2$CH), 3.39 (2H, s, F$_2$PhCH$_2$), 2.80-2.76 (2H, d, J=11.1 Hz, N(CH$_2$)$_2$), 2.60-2.55 (2H, t, J=7.0 Hz, NCH$_2$), 1.93-1.86 (2H, t, J=11.1 Hz, N(CH$_2$)$_2$), 1.62-1.58 (2H, d, J=12 Hz), 1.49-1.42 (2H, q, J=6.3 Hz, NCH$_2$CH$_2$), 1.35-1.31 (1H, m, NCH$_2$CH$_2$CH(CH$_2$)$_2$), 1.26-1.19 (2H, t, J=12.0 Hz). The free base was converted into its HCl salt, m.p.=280-281° C. Anal: (C$_{17}$H$_{30}$N$_2$F$_2$·2HCl·0.25H$_2$O) Calculated: C, 65.12; H, 6.85; N, 5.62; Found: C, 65.13; H, 6.80, N, 5.28.

EXAMPLE 9

4-[2-((Diphenylmethyl)amino)ethyl]-1-(phenylmethyl)piperidine

Compound 4-[2-(diphenylmethyl)aminocarbonyl)methyl-1-(phenylmethyl)piperidine (0.54 g, 1.31 mmol) was reacted with 1M BH$_3$/THF (5.0 ml) in THF (10 ml) to produce 4-[2-(diphenylmethyl)amino]ethyl-1-(phenylmethylpiperidine, 0.44 g (84% yield)(procedure E). $^1$H NMR (CD$_3$Cl) δ 7.39-7.19 (15H, m, Ar—H), 4.79 (1H, s, PhCH), 3.47 (2H, s, PhCH), 2.86-2.82 (2H, d, J=11.1 Hz, N(CH$_2$)$_2$), 2.59-2.55 (2H, t, J=7.2 Hz, NCH$_2$), 1.94-1.87 (2H, t, J=11.1 Hz, N(CH$_2$)$_2$), 1.61-1.58 (2H, m), 1.48-1.42 (2H, m), 1.34-1.20 (3H, m). The free base was converted into its HCl salt, m.p. −172-174° C. Anal: (C$_{27}$H$_{32}$N$_2$·2HCl·106H$_2$O) Calculated: C, 68.05; H, 7.64; N, 5.88; Found: C, 68.06; H, 7.82; N, 5.90.

EXAMPLE 10

4-[2-((Diphenylmethyl)-N-methylamino)ethyl]-1-(4-phenylmethyl)piperidine

A solution of 4-[(2-Diphenylethyl)aminomethyl]-1-[(4-fluorophenyl)methyl]piperidine (0.23 g, 0.59 mmol), formaldehyde (1.0 g, 37%/H$_2$O) and formic acid (2.0 g, 88%/H$_2$O) was refluxed for 3 hours. After the reaction solution was cooled to room temperature, the solvent was removed under vacuo. The crude product was purified by chromatography (EtOAc/Hexane=1/2) to give a white solid 0.17 g (71% yield). $^1$H NMR (CD$_3$Cl) δ 7.40-7.16 (12H, m, Ar—H), 7.05-6.95 (2H, t, J=7.4 Hz, Ar—H), 4.31 (1H, s, Ph$_2$CHN), 3.41 (2H, s, p-FPhCH$_2$N), 2.80-2.76 (2H, d, J=11.8 Hz, N(CH$_2$)$_2$), 2.36-2.30 (2H, t, J=7.5 Hz, NCH$_2$), 2.11 (3H, s, NCH$_3$), 1.91-1.83 (2H, t, J=11.4 Hz, N(CH$_2$)$_2$), 1.54-1.50 (2H, d, J=11.4 Hz), 1.47-1.40 (3H, m, NCH$_2$CH$_2$CH), 1.32-1.10 (2H, m). The free base was converted into its HCl salt, m.p.=260-261° C. Anal. [C$_{28}$H$_{33}$N$_2$F·2HCl·0.50H$_2$O]] Calculated: C, 67.46; H, 7.29; N, 5.61; Found: C, 67.33; H, 7.19; N, 5.56.

EXAMPLE 11

4-[[2-(Diphenyl)ethyl]aminomethyl]-1-[(4-fluorophenyl)methyl]piperidine

Compound 4-[(2-diphenylethyl)aminocarbonyl]-1-[(4-fluorophenyl)methyl]piperidine (0.32 g, 13 mmol) was reacted with 1M BH$_3$/THF (4.0 ml) in THF (20 ml) to produce 4-[(2-diphenylethyl)aminomethyl]-1-[(4-fluorophenyl)methyl]piperidine, 0.25 g (81% yield)(procedure E). $^1$H NMR (CD$_3$Cl) δ 7.32-7.19 (12H, m, Ar—H), 7.00-695 (2H, m, Ar—H), 4.21-4.17 (1H, t, J=7.7 Hz, (Ph$_2$CH), 3.67 (1H, s, NH), 3.41 (2H, s, p-FPhCH$_2$), 3.22-3.19 (2H, d, J=7.8 Hz, NHCH$_2$CH(Ph)$_2$), 2.83-2.79 (2H, bd, J=11.1 Hz, N(CH$_2$)$_2$), 2.52-2.50 (2H, d, J=6.6 Hz, NHCH$_2$CH), 1.91-1.84 (2H, t, J=11.1 Hz), 1.58-1.54 (2H, d, J-12 Hz), 1.45-1.39 (1H, m, NHCH$_2$CH), 1.21-1.14 (2H, t, J=12 Hz). The free base was converted into its HCl salt, m.p.=126-127° C. Anal. [C$_{27}$H$_{31}$FN$_2$O·2HCl] Calculated: C, 62.96; H, 7.31; N, 5.43; Found: C, 62.93; H, 7.19; N, 5.41.

EXAMPLE 12

4[(Bis(4-fluorophenyl)methylamino)methyl]-1-[2-(phenyl)ethyl]piperidine

Compound 4-[(2-diphenylethyl)aminomethyl]-1-[(4-fluorophenyl)methyl]piperidine (0.30 g, 0.71 mmol) was reacted with 1M BH$_3$/THF (4. ml) in NMR (25 ml) to produce a white solid 4-[(bis(4-fluorophenyl)methylamino)methyl]-1-(phenylethyl)piperidine, 0.28 g (96% yield)(procedure E). $^1$H NMR (CD$_3$Cl) δ 7.35-7.18 (10H, m, Ar—HO, 7.00-6.95 (3H, m, Ar—H), 4.74 (1H, S, P-FPh)$_2$CH), 3.02-2.99 (2H, d, J=10.8 Hz, N(CH$_2$)$_2$), 2.83-2.78 (2H, M), 2.60-2.55 (2H, m), 2.45-2.43 (2H, d, J=6.2 Hz, NHCH$_2$CH), 2.04-1.96 (2H, t, J=11.4 Hz, N(CH$_2$)$_2$), 1.78-1.26 (5H, m). The free base was converted into its HCl salt, m.p.=214-215° C. Anal. (C$_{27}$H$_{30}$F$_2$N$_2$·2HCl·0.50H$_2$O) Calculated: C, 64.58; H, 6.61; N, 5.57; Found: C, 64.61; H, 6.65; N, 5.43.

EXAMPLE 13

[[(2-(Diphenyl)ethyl]-N-methylaminomethyl]-1-[(4-fluorophenyl)methyl]piperidine 4-[(2-Diphenylethyl)aminomethyl]-1[)4-fluorophenyl)methyl]-piperidine 4-[(2-diphenylethyl)aminomethyl]-1-[(4-fluorophenyl)methyl]piperidine (45 mg, 0.11 mmol) was refluxed in formaldehyde (1.0 g) and formic acid (2.0 g, 37%/H$_2$O) to produce 4-[(2-diphenylethyl)-N=methylaminomethyl]-1-[(4-fluorophenyl)methyl]piperidine, 44 mg (88% yield)(procedure F). $^1$H NMR (CD$_3$Cl) δ 7.28-7.13 (12H, m, Ar—H), 7.02-6.96 (2H, t, J=8.4 Hz, Ar—H), 4.15-410 (1H, t, J=7.5 Hz, Ph$_2$CH), 3.46 (2H, s, F-PhCH$_2$), 2.91-2.88 (2H, d, J=7.5 Hz, Ph$_2$CHCH$_2$N), 2.81-2.77 (2H, d, J=1.1 Hz, N(CH$_2$)$_2$), 2.20 (3H, s, CH$_3$), 2.20-2.17 (2H, d, J=7.5 Hz, NCH$_2$CH), 1.90-1.83 (2H, t, J=11.4 Hz, N(CH$_2$)$_2$), 1.52-1.47 (2H d, J=12.9 Hz), 1.54-1.28 (1H, m, NCH$_2$CH), 1.14-1.06 (2H, t, J=12.4 Hz). The free base was converted into its oxalate salt, m.p.=144-145° C. Anal.

EXAMPLE 14

4-[2-[(1-(phenyl)ethyl)amino]ethyl]-1-[(4-fluorophenyl)methyl]piperidine

Compound 4-[(1-phenylethyl)aminocarbonyl]methyl-1-[(4-fluorophenyl)methyl]piperidine (0.33 g, 0.93 mmol) was reacted with 1M BH$_3$/THF (5.0 ml) to produce a viscous oil, 0.23 g (95% yield)(procedure E). $^1$H NMR (CD$_3$Cl) δ 7.34-=7.21 (5H, m, Ar—H), 7.01-6.95 (2H, t, J=8.4 Hz, Ar—H), 4.09-4.07 (1H, d, J=6.0 Hz, NH), 3.77-3.71 (1H, q, J=6.3 Hz, PhCHMe), 3.42 (2H, s, p-FPhCH$_2$), 2.82-2.78 (2H, d, J=10.8 Hz; N(CH)$_2$), 2.55-2.37 (2H, m, NCH$_2$), 1.91-1.83 (2H, t, J=11.4 Hz, N(CH)$_2$), 1.59-1.53 (4H, m), 1.44-1.38 (1H, m), 1.36-1.34 (3H, d, J=6.0 Hz, CH$_3$), 1.25-1.14 (2H, m), The free base was converted into its oxalate salt, m.p.=172-173° C. Anal. [C$_{22}$H$_{29}$FN$_2$·2(COOH)$_2$] Calculated: C, 59.99; H, 6.39; N, 5.38; Found C, 59.84; H, 6.46; N, 5.29.

EXAMPLE 15

Synthesis of Racemic cis- and trans-2-Diphenylmethyl-5-(4-fluorobenzylamino)piperidine To a room temperature solution of 420 mg racemic cis- and trans-2-diphenylmethyl-5-aminopiperidine (1.58 mmol), 156 mg 4-fluorobenzaldehyde (0.8 equiv), 94 mg glacial HOAc (1 equiv) in 30 mL 1,2-dichloroethane was added portionwise 119 mg sodium cyanoborohydride (1.2 equiv). The mixture was stirred for 18 hours. Then, H$_2$O was added and the mixture stirred for 30 min, then acidified with conc HCl, and stirred another 30 min. Then the mixture was basified with conc NaOH and extracted thrice with CH$_2$Cl$_2$. The organic phases were collected, dried (MgSO$_4$) and evaporated. The residue was chromatographed (SiO$_2$; CH$_2$Cl$_2$; MeOH) to purify the mixture (240 mg, 40%) of both diastereomeric pairs. Then this mixture was further chromatographed (SiO$_2$; 1 hexane; 1 EtOAc: 0.06 triethylamine) to separate the diastereomers. Eluting first: $^1$H, NMR, (CDCl$_3$; 400 MHz) δ 1.3-1.4 (2H, m, H-3), 1.49 (1H, tt, $^2$J and $^3$J$_{3a}$=13.6 Hz; $^3$J$_{3e}$ and $^3$J$_{5e}$=4.0 Hz, H-4ax), 1.65-1.85 (3H, m, H4ax 2NH), 2.65-2.72 (2H, m, H-5eq, H-6ax), 2.99 (1H, d, $^2$J=10.4 Hz, H-6eq), 3.28 (1H, dt, $^3$J=4.4 and 10.8 Hz, H-2ax), 3.71 (2H, s, CH$_2$C$_6$H$_4$F), 3.81 (1H, d, $^3$J=9.6 Hz, CH(C$_6$H$_5$)$_2$), 6.99 (2H, t, $^3$J=8.4 Hz, ArH ortho F), 7.12-7.39 (12H, m, ArH). Precipitated as bis-hydrochloride salt. mp 60-105° C. Elemental analysis calculated for C$_{25}$H$_{29}$N$_2$FCl$_2$·0.5 H$_2$O: C, 65.93; H1 6.59; N, 6.15. Found: C, 65.26; H, 6.78; N, 6.49.

Eluting second: racemic trans-2-diphenylmethyl-5-(4-fluorobenzylamino)piperidine (96 mg, 38.5%), $^1$H NMR (CDCl$_3$; 400 MHz) δ 1.17 (2H, qm, $^3$J=10 Hz, H-3ax and H4ax), 1.57-1.65 (1H, m, H-3eq), 1.4-1.7 (bs, NH), 1.9-1.96 (1H, m, H-4eq), 2.33 (1H, t, $^2$J and $^3$J=10.4 Hz, H-6ax), 2.65 (1H, m, Σ$^3$ J=36 Hz, H-5ax), 3.15-3.25 (2H, m, H-2ax, H-6eq), 3.68 (1H, d, $^2$J=0.6 Hz, CH(C$_6$H$_5$)$_2$), 3.75 (2H, s, CH$_2$C$_6$H$_4$F), 6.97 (2H, t, $^3$J=8.8 Hz, ArH Ortho F), 7.1-7.3 (10H, m, ArH), 7.36 (2H, d, $^3$J=7.6 Hz, ArH meta F). Precipitated as bis-hydrochloride salt. Elemental analysis calculated for C$_{25}$H$_{29}$N$_2$FCl$_2$·0.5 H$_2$O: C, 65.93; H, 6.59; N, 6.15. Found: C, 65.56; H, 6.89; N, 6.14

EXAMPLE 16

Synthesis of racemic trans-3-hydroxy-4-[2-diphenylmethoxy)ethyl]-1-[(4-fluorophenyl)methyl]piperidine To a stirred suspension of

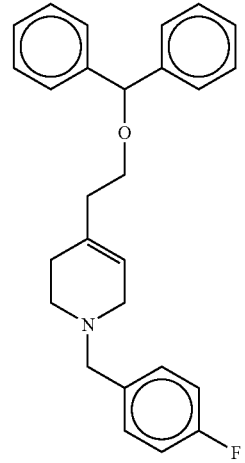

(0.92 g, 1.9 mmol) in THF (10 mL) cooled to 0° C. was added dropwise 1M BH$_3$ tetrahydrofuran complex (7.7 mL, 7.7 mmol, 4 equiv). Afterwards, the cooling bath was removed and the solution allowed to warm to RT. The mixtures was then refluxed for 12 hr. After cooling to 0° C., H$_2$O (5.76 mL), EtOH (5.76 mL) and 3N NaOH (15 mL) were added followed by dropwise addition of 30% H$_2$O$_2$ (18 mL). The reaction was stirred at 55° C. for 12 hours then cooled to RT and extracted thrice with CH$_2$Cl$_2$. The extracts were pooled, dried (MgSO$_4$) and evaporated to a clear oil. The crude product was chromatographed (SiO$_2$; 5% MeOH/CH$_2$Cl$_2$) to furnish the free base (0.553 mg, 71%). $^1$H NMR (CDCl$_3$) ∂ 1.34-1.39 (2H, m), 1.59-1.55 (2H, m), 1.81-1.95 (3H, m), 2.72 (1H, d, J=9.9 Hz), 2.98 (1H, d, J=10.5 Hz), 3.42-3.63 (5H, m), 5.37 (1H, s), 6.98 (2H, t, J=9.3 Hz), 7.22-7.35 (12H, m). This was then reacted in EtOH (5 mL) with oxalic acid dihydrate (0.169 g, 1.1 equiv) to furnish the title compound (468 mg, 77%). mp 143-50° C. Elemental analysis calculated for C$_{28}$H$_{31}$NO$_6$F: C, 68.37; H, 6.29; N, 2.75. Found: C, 67.96; H, 6.43; N, 2.63.

EXAMPLE 17

Synthesis of racemic trans-3-Propionyl-4-[2-(diphenylmethoxy)ethyl]-1-[(4-fluorophenyl)methyl]piperidine To a solution of 61 mg 3-hydroxy-4-[2-(diphenylmethoxy)ethyl]-1-[(4-fluorophenyl)methyl]piperidine (0.15 mmol) and 21 mg triethylamine (0.23 mmol, 1.5 equiv) in 2 mL CH$_2$Cl$_2$ cooled in an ice bath was added dropwise 18 mg propionyl chloride (0.19 mmol, 1.3 equiv) and the reaction was allowed to warm to RT. After 1 hr, the same quantities of triethylamine and propionyl chloride were added. After 1 hr, H$_2$O was added and the organic layer was separated, dried (MgSO$_4$) and evaporated. The remaining residue was chromatographed (SiO$_2$; CH$_2$Cl$_2$/MeOH) to yield the title compound as the free base (53 mg, 77%). 1H NMR (CdCl$_3$ ∂ 1.1 (3H, t, J=8.1 Hz), 1.26-1.95 (7H, m), 2.26 (2H, q, J=7.2 and 7.5 Hz), 2.71 (1H, d, J=11.7 Hz), 3.02 (1H, d, J=10.5 Hz), 3.41-3.52 (4H, m), 4.67 (1H, t, J=9.6 Hz), 5.31 (1H, s), 6.98 (2H, t, J=9.3 Hz), 7.2-7.4 (12H, m). This was then reacted in a mixture of 2 mL 50% EtOH/Et$_2$O with oxalic acid dihydrate (15.4 mg, 1.1 equiv) to furnish the title compound. mp ° C. Elemental analysis calculated for $C_{32}H_{36}NO_7F \cdot 0.5\ H_2O$: C, 67.43; H, 6.41; N, 2.46. Found: C, 67.34; H, 6.43; N, 2.44.

EXAMPLE 18

Synthesis of racemic 3-Keto-4-[2-(diphenylmethoxy) ethyl]-1-[(4-fluorophenyl)methyl]piperidine To a solution of oxalyl chloride (0.4 mmol, 0.87 equiv) in CH$_2$Cl$_2$ (3 mL) cooled to –78° C. was added dropwise 108 mg dimethylsulfoxide (1.38 mmol, 3 equiv). The mixture was stirred for 10 min and a solution of 236 mg racemic trans-3-hydroxy-4-[2-(diphenylmethoxy)ethyl]-1-[(4-fluorophenyl) methyl]piperidine (0.46 mmol) in CH$_2$Cl$_2$ (1 mL) was added dropwise. After stirring 15 min, triethylamine (825 mg, 17.6 equiv) was added and the mixture was allowed to warm to room temperature. All volatiles were evaporated at room temperature and the remaining residue was chromatographed (SiO$_2$; hexane:EtOAc:MeOH) to furnish the free base (116 mg, 60%), which decomposes at room temperature and must be stored in the cold. $^1$H NMR (CdCl$_3$) $\partial$ 1.45-1.65 (2H, m), 2.0-2.1 (1H, m), 2.2-2.3 (1H, m), 2.38-2.6 (2H, m), 2.77 (1H, d, J=13.6 Hz), 2.9 (1H, bd, J=13.6 Hz), 3.45-3.55 (4H, m), 5.30 (1H, s), 6.99 (2H, t, J=11.2 Hz), 7.19-7.39 (12H, m). The title compound (125 mg, 50%) was furnished by reacting the free base (205 mg) with oxalic acid dihydrate (62 mg, 1 equiv). mp 104-9° C. Elemental analysis calculated for $C_{29}H_{30}NO_6F$: C, 68.64; H, 5.92; N, 2.76. Found: C, 68.34; H, 5.93; N, 2.68.

EXAMPLE 19

Synthesis of 4-[2-(diphenylmethoxy)ethyl]-1-[(4-iodophenyl)methyl]piperidine

4-[2-(diphenylmethoxy)ethyl]piperidine (0.23 g, 0.77 mmol) was reacted with 4-iodo benzyl bromide (0.76 g, 2.5 mmol) and K$_2$CO$_3$ (1.00 g, 7 mmol) in EtOH (10 mL) to give a thick oil, 0.17 g (%). 1H NMR (300 MHz, CDCl3): 1.21-1.63 (7H, m), 1.87-1.93 (t, J=11 Hz, 2H, N(CH2)-), 2.79-2.83 (bd, J=12 Hz, 2H, N(CH2)-), 3.41-3.49 (4H, m), 5.31 (s, 1H, Ph2CHO-), 7.05-7.63 (14H, m, ArH). Free base was converted into its oxalate sale, m.p.=160-161° C. Anal. $C_{27}H_{30}INO$. $(COOH)_2$.

Biological Testing

We have surprisingly discovered that longer aromatic-alkyl chains in piperidine derivatives give rise to more interaction with the serotonin transporter (SERT), and hence less selectivity (c.f. A. K. Dutta et al., "Structure-Activity Relationship Studies of Novel 4-[2-[Bis(4-fluorophenyl)methoxy]ethyl]-1-(3-phenylpropyl)piperidine Analogs: Synthesis and Biological Evaluation at the Dopamine and Serotonin Transporter Sites", J. MED. CHEM., 1996, 39, 749-756; A. K. Dutta et al., "Highly Selective, Novel Analogs of 4-[2-(diphenylmethoxy)ethyl]-1-benzylpiperidine For The Dopamine Transporter: Effect of Different Aromatic Substitutions on Their Affinity and Selectivity", J. MED. CHEM., 1997, 40, 35-43; A. K. Dutta et al., Potent and Selective Ligands for the Dopamine Transporter (DAT): Structure-Activity Relationship Studies of Novel 4-[2-diphenylmethoxy) ethyl]-1-3-phenylpropyl)piperidine Analogs", J. MED. CHEM., 1998, 41, 699-705). In an effort to explore the effect of electronegative fluorine atoms and the strong electron withdrawing group CN, the compounds of Examples 1-4 were designed and synthesized. The presence of electronegative and electron withdrawing groups enhanced the activity and selectivity of these analogs. These novel compounds, with but a methylene group between the piperidine N-atom and the aryl ring, and with an electronegative aryl substituent, exhibited profound selectivity and potency for the dopamine transporter (DAT). Thus, the compound of Example 4 with a strong electron withdrawing cyano group present in the phenyl ring exhibited remarkable potency and selectivity (IC50, 3.7 nM, SERT/DAT=615, Table 1) for the dopamine transporter. This is a remarkable improvement over the standard reference compound GBR 12909 (IC50, 14 nM, SERT/DAT=6). The compound of Example 2 also showed good potency and more selectivity than GBR 12909 for the DAT (SERT/DAT=122).

The compounds of Examples 8, 9, 11 and 12 (Table 1) employ a 4-(aminoalkyl) linkage between the piperidine ring and the bisaromatic methane portion of the molecule rather than an oxyalkyl linkage. Both Examples 8 and 9 are more potent and selective than the standard GBR 12909 molecule (IC50, 7.0 and 4.5 nM, respectively); SERT/DAT=227 and 347, respectively). The compound 4-[2-(diphenylmethoxy) ethyl]-1-[(4-iodophenyl)methyl]piperidine sets a new standard of activity.

In the compound of Example 11 where the N-atom was relocated to an adjacent position, an interesting effect consisting of the strong affinity for the DAT and the moderate affinity for the SERT was observed. Compound with such dual activity might find unique applications in the medication development for drug abuse and in other neurological disorders, including treatment of depression.

None of these compounds developed in this current series showed any appreciable activity for the norepinephrine transporter (NET), which demonstrates their selectivity for the DAT.

The current novel compounds were also evaluated in the dopamine reuptake inhibition assay which measures the extent of inhibition of dopamine reuptake in the cytosol by these novel compounds. In this regard, cocaine and GBR 12909 are potent DA uptake inhibitors. Ideally, a desirable drug for the treatment of drug addiction should possess less dopamine uptake inhibitory potency and should be less potent than GBR 12909 in that regard, which will increase the drug's chances to act as cocaine antagonist. In this current series of compounds, Table 2, all of the listed results reflect an increased potential of these novel compounds to act as cocaine antagonists than GBR 12909.

TABLE 1

Affinity and Selectivity of Drugs at the Dopamine (DAT), Serotonin (SERT) and Norepinephrine (NET) Transporters

| Compound | DAT, IC$_{50}$, nM | SERT, IC$_{50}$, nM | NET, IC$_{50}$, nM | DAT/SERT |
|---|---|---|---|---|
| CFT | 32.3 ± 2.6 | | | |
| GBR 12909 | 10.6 ± 1.9 | 132.0 ± 0.0 | 496 ± 22 | 12 |
| Example 1 | 23.4 ± 3.8 | 1145.7 ± 43.4 | | 49 |
| Example 2 | 10.1 ± 0.9 | 1221 ± 139.4 | | 122 |
| Example 3 | 32.1 ± 2.1 | 2262.8 ± 144.1 | | 71 |
| Example 4 | 3.7 ± 0.6 | 2277 ± 470 | | 615 |
| Example 5 | 2156 ± 54 | >1,000 | | |
| Example 6 | 26.6 ± 1.4 | 585.6 ± 29.2 | | 22 |
| Example 7 | 34.4 ± 4.2 | 625.8 ± 33 | 691 ± 68 | 19 |
| Example 8 | 7.0 ± 1.7 | 1587 ± 160 | 1,027 ± 94 | 227 |

TABLE 1-continued

Affinity and Selectivity of Drugs at the Dopamine (DAT), Serotonin (SERT) and Norepinephrine (NET) Transporters

| Compound | DAT, $IC_{50}$, nM | SERT, $IC_{50}$, nM | NET, $IC_{50}$, nM | DAT/SERT |
|---|---|---|---|---|
| Example 9 | 4.5 ± 0.6 | 1562 ± 208 | 2,623 ± 173 | 347 |
| Example 10 | 213 ± 3 | 1659 ± 469 | | 8 |
| Example 11 | 19.7 ± 1.4 | 137.2 ± 45.6 | 1,111 ± 119 | 7 |
| Example 12 | 65.3 ± 3.2 | 1098 ± 245.6 | | 17 |
| Example 13 | 94.0 ± 12.5 | 2524 ± 230 | | 27 |
| Example 14 | 295.4 ± 40.9 | 963 ± 38.5 | | |
| —[1] | 751.0 ± 61.6 | 5855.7 ± 594.6 | | |
| 3-OH[2] | 14.3 ± 3.7 | 984 ± 94 | 678 ± 13 | 69 |
| Example 19 | 0.96 ± 0.16 | 2920 ± 432 | 1151 ± 116 | 3041 |

[1] 4-[((1-phenylethoxy)ethyl]-1-[(4-fluorophenyl)methyl]piperidine
[2] 4-[2-(diphenylmethoxy)ethyl]-1-[(3-hydroxyphenyl)methyl]piperidine
[3] 4-[2-(diphenylmethoxy)ethyl]-1-[4-iodophenyl)methyl]piperidine

TABLE 2

Inhibition of Dopamine Reuptake in Rat Synaptosome Tissue

| Compound | [3H]DA Inhibition, IC50 (nM) | [3H]DA/Binding, IC50 |
|---|---|---|
| GBR 12909 | 6.63 ± 0.43 | 0.62 |
| Example 2 | 12.03 ± 1.62 | 1.33 |

TABLE 3

Binding Activity of Cis and Trans at the Dopamine, Serotonin and Norepinephrine Transporters

| Compound | DAT, $IC_{50}$, nM [³H]WIN 35,428 | SERT, $IC_{50}$, nM [³H]citalopram | NET, $IC_{50}$, nM [³H]nisoxetine | [³H]DA uptake Inhibition, $IC_{50}$ (nM) |
|---|---|---|---|---|
| (±)-7a | 30.00 ± 0.5 | 2,813 ± 411 | 1,349 ± 190 | 28.9 ± 2.5 |
| (±)-7b | 212 ± 20 | 1,333 ± 102 | 4,468 ± 1,181 | 106 ± 10 |

TABLE 4

Selectivity of Various Ligands for their Binding to the Monoamine Transporters

| Compound | SERT/DAT | NET/DAT | [³H]DA/DAT Binding |
|---|---|---|---|
| Cocaine | 2.7 | 6.36 | |
| Example 11 | 6.9 | 5.6 | 2.5 |
| (±)-7a | 93.7 | 44.9 | 0.03 |
| (±)-7b | 6.28 | 21 | 0.5 |

TABLE 5

Affinity and Selectivity of Drugs at the Dopamine, Serotonin and norepinephrine Transporters in Rat Striatum

| Compound | DAT, $IC_{50}$, nM, [³H]WIN 35,428[a] | SERT, $IC_{50}$, nM [³H]citalopram[a] | NET, $IC_{50}$, nM [³H]nisoxetine[a] | SERT/DAT |
|---|---|---|---|---|
| Cocaine | 266 ± 37 | 737 ± 160 | 3,526 ± 554 | 2.7 |
| GBR 12909 | 10.6 ± 1.9 | 132 ± 0 | 496 ± 22 | 12 |
| Example 16 | 5.96 ± 1.26 | 1,108 ± 477 | 637 ± 114 | |
| Example 18 | 99 ± 18 | 7,747 ± 1618 | 6,299 ± 694 | |
| Example 17 | 583 ± 81 | 177,800 ± 53,000 | 35,806 ± | |

TABLE 2-continued

Inhibition of Dopamine Reuptake in Rat Synaptosome Tissue

| Compound | [3H]DA Inhibition, IC50 (nM) | [3H]DA/Binding, IC50 |
|---|---|---|
| Example 4 | 4.58 ± 0.80 | 1.23 |
| Example 7 | 16.6 ± 2.8 | 0.48 |
| Example 6 | 9.7 ± 1.2 | 0.36 |
| Example 11 | 49.56 ± 7.2 | 2.5 |
| Example 9 | 20.6 ± 2.5 | 4.5 |
| Example 8 | 10.7 ± 1.8 | 1.5 |

The activities of racemic cis- and trans-isomers of the compounds of Example 15 were measured. The results are presented below in Table 3. The selectivities with respect to SERT/DAT, NET/DAT and [3H] DA/DT binding ratios are presented in Table 4, along with similar data for cocaine and subject invention Example 11. As can be seen, there is a significant change in the selectivity as between the cis- and trans-isomers. It is expected that the individual stereoisomers of each pair of geometric isomers will also exhibit quite different activity.

What is claimed is:

1. Compounds exhibiting CNS activity in mammalian species, said compounds having the formula:

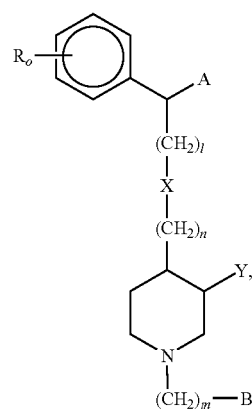

(I)

wherein A in formulae (I) is

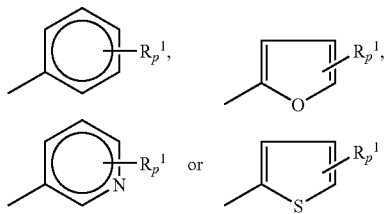

B is

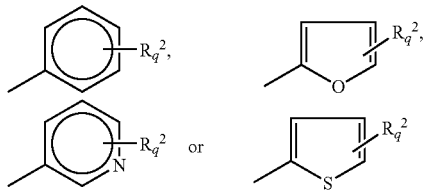

X is selected from the group consisting of N, —NH—, —NR$^4$—, —O—, and —S—; R$^4$ is C$_{1-4}$ alkyl, NH$_2$, C$_{1-4}$ hydroxyalkyl, halogenated C$_{1-4}$ alkyl, C$_{2-4}$ alkenyl, C$_{2-4}$ hydroxyalkenyl, halogenated C$_{2-4}$ alkenyl, C$_{2-4}$ and alkynyl, and C$_{2-4}$ halogenated alkynyl; Y is -NH$_2$, -OH, =O, or-O-C(O)-R$^5$;

l is 0, 1, or 2 ;
n is 1 or 2;
m is 1 or 2;
o is 0, 1, 2, 3, or 4;
p is 0, 1, 2, 3, or 4;
q is 0, 1, 2, or 3;
r is an integer from 0 to 5
R, R$^1$, and R$^2$ are selected from the group consisting of H, F, Cl, Br, I, CN, COOEt, OH, NO$_2$, NH$_2$, OR$^5$, wherein R$^5$ is C$_{1-8}$ alkyl, C$_{5-6}$ cycloalkyl, or C$^{2-8}$ alkenyl or R$^2$ is a 5 or 6 membered heterocycle,

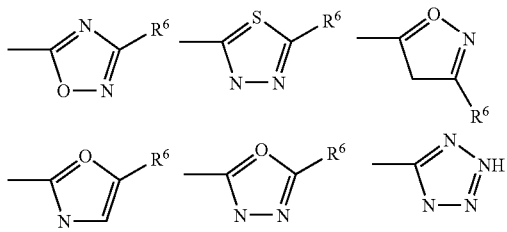

and where any carbon of CH$_2$ m may be substituted by OR$^7$ where R$^7$ is C$_{1-18}$ alkyl or C$_{2-18}$ alkylene, or

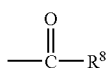

where R$^8$ is C$_{1-18}$ alkyl or C$_{2-18}$ alkylene, or a pharmaceutically acceptable salt or derivative thereof.

2. A compound of claim 1, wherein l=0, n=2.
3. A compound of claim 1, wherein l=0, n =2, m=L
4. A compound of claim 1, wherein X is —NH— or —O—.
A-is- 5. A compound of claim 4, wherein l=0, n =2, m =1, and p=1.
6. A compound of claim 1, selected from the group consisting of, trans-3-hydroxy-4-[2-diphenylmethoxy)ethyl] -1-[(4-fluorophenyl)methyl] piperidine, trans-3-propionyl-4-[2-(diphenylmethoxy)ethyl] -1 -[(4-fluorophenyl)methyl] piperidine, 3-keto-4-[2-(diphenylmethoxy)ethyl] -1 -[(4-fluorophenyl)methyl] piperidine, and the pharmaceutically acceptable salts and derivatives thereof.
7. The compound of claim 1 having the structure:

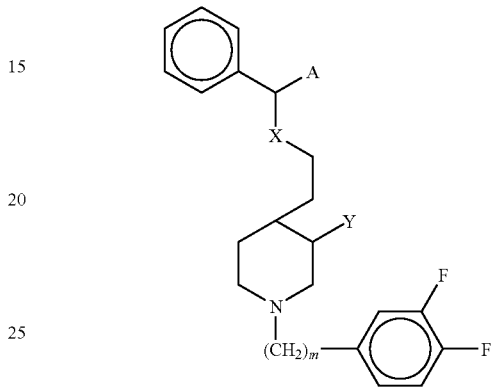

wherein A is

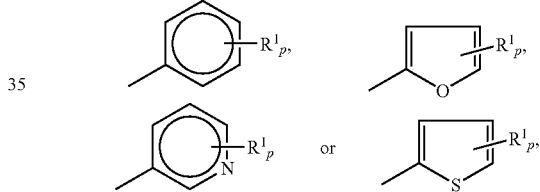

and where X is selected from the group consisting of —NH—, —NR$^4$—, and —O—;
R$^4$ is C$_{1-4}$ alkyl, NH$_2$, C$_{1-4}$ hydroxyalkyl, halogenated C$_{1-4}$ alkyl, C$_{2-4}$ alkenyl, C$_{2-4}$ hydroxyalkenyl, halogenated C$_{2-4}$ alkenyl, C$_{2-4}$ and alkynyl, and C$_{2-4}$ halogenated alkynyl;
Y is —H, -NH$_2$, —OH, =O, or—O—C(o)-R$^5$;
wherein R$^5$ is C$_{1-8}$ alkyl, C$_{5-6}$ cycloalkyl, or C$_{2-8}$ alkenyl or R$^5$ is a 5 or 6 membered heterocycle;
m is 1 or 2;
p is 0, 1, 2, 3, or 4;
R1 is selected from the group consisting of H, F, Cl, Br, I, CN, COOEt, OH, NO$_2$, NH$_2$, OR$^5$, wherein R$^5$ is C$_{1-8}$ alkyl, C$_{5-6}$ cycloalkyl, or C$_{2-8}$ alkenyl or R$^2$ is a 5 or 6 membered heterocycle,
and where any carbon of CH$_2$m may be substituted

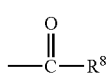

by OR$^7$ where R$^7$ is C$_{1-18}$ alkyl or C$_{2-18}$ alkylene, or
where R$^8$ is C$_{1-18}$ alkyl or C$_{2-18}$ alkylene,
or a pharmaceutically acceptable salt or derivative thereof.

8. A compound of claim 1, selected from the group consisting of:
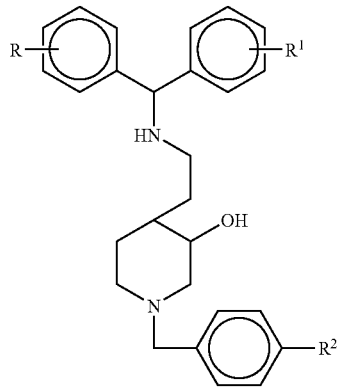
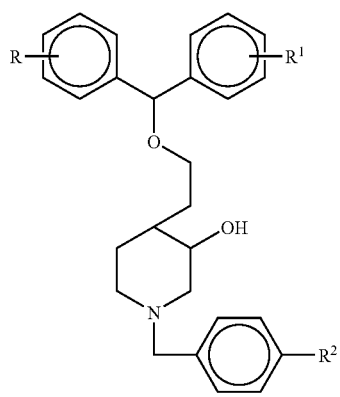
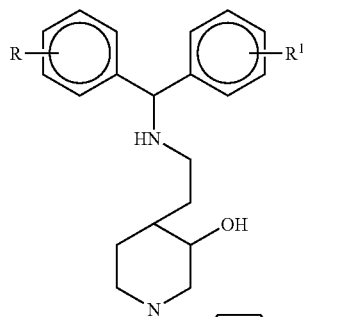
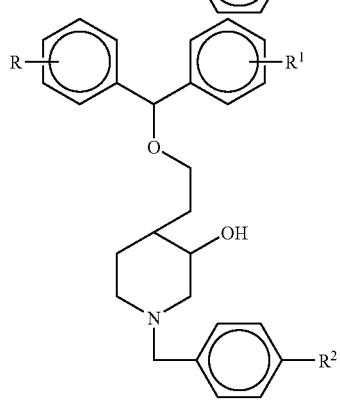
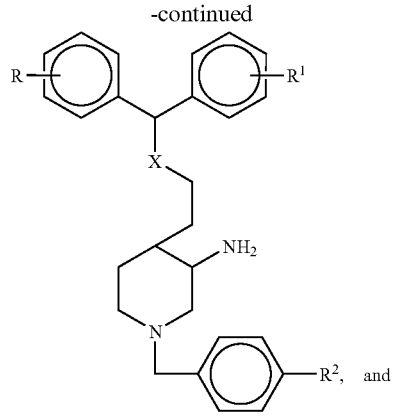
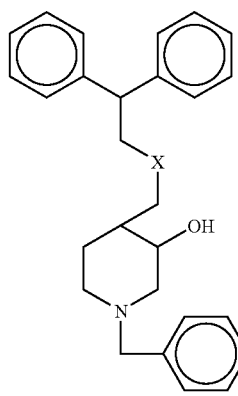
and pharmaceutically acceptable salts and derivatives thereof.
9. The compound of claim 1, having the structure:
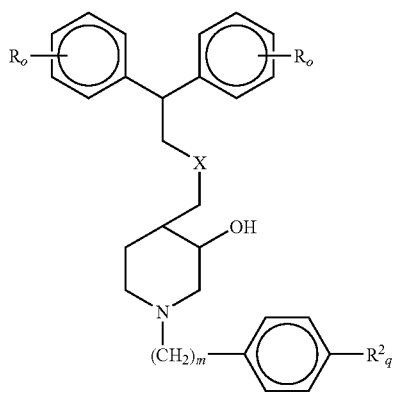
and pharmaceutically acceptable salts and derivatives thereof.

10. A compound exhibiting CNS activity in mammalian species, having the formula:

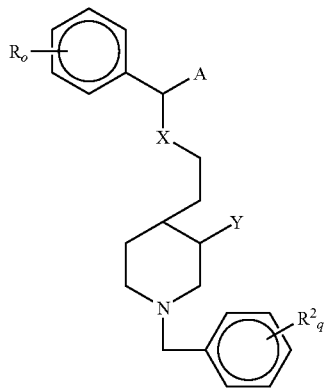

wherein A is

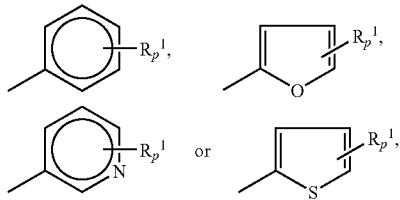

and where X is selected from the group consisting of —NH—, —NR⁴—, and —O—; R⁴ is $C_{1-4}$ alkyl, $NH_2$, $C_{1-4}$ hydroxyalkyl, halogenated $C_{1-4}$ alkyl, $C_{2-4}$ alkenyl, $C_{2-4}$ hydroxyalkenyl, halogenated $C_{2-4}$ alkenyl, $C_{2-4}$ and alkynyl, and $C_{2-4}$ halogenated alkynyl; Y is —OH, $OR^9$, $NH_2$, or $NHR^9$ wherein $R^9$ is wherein $R^{10}$ is $C_{6-20}$ alkyl,

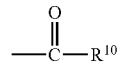

o is 0, 1, 2, 3, or 4; R, $R^1$ and $R^2$ are selected from the group consisting of H, F, Cl, Br, I, CN, COOEt, OH, $NO_2$, $NH_2$, $OR^5$; wherein $R^5$ is $C_{1-8}$ alkyl, $C_{5-6}$ cycloalkyl, or $C_{2-8}$ alkenyl or $R^2$ is a 5 or 6 membered heterocycle; p is individually 0, 1, or 2, q is 0, 1, 2, or 3 wherein at least one $R^2$ is an electron withdrawing group, and pharmaceutically acceptable salts and derivatives thereof.

11. A compound having the following formula:

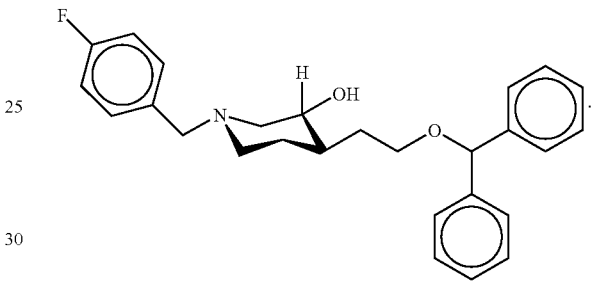

* * * * *

UNITED STATES PATENT AND TRADEMARK OFFICE
CERTIFICATE OF CORRECTION

PATENT NO. : 7,595,331 B2
APPLICATION NO. : 11/007484
DATED : September 29, 2009
INVENTOR(S) : Aloke K. Dutta It is certified that error appears in the above-identified patent and that said Letters Patent is hereby corrected as shown below:

Column 33, Line 40, Claim 1:

After "cycloalkyl, or"

Delete: "$C^{2-8}$ alkenyl" and insert: -- $C_{2-8}$ alkenyl --.

Column 33, Line 54, Claim 1:

After "any carbon of"

Delete: "$CH_2$ m" and insert: -- $(CH_2)_m$ --.

Column 33, Line 64, Claim 3:

After "n = 2,"

Delete: "m = L" and insert: -- m = 1 --.

Column 33, Line 67, Claim 4:

After "X is -NH- or -O-"

Delete: "A-is-".

Signed and Sealed this

Twenty-fifth Day of May, 2010

David J. Kappos
*Director of the United States Patent and Trademark Office*

CERTIFICATE OF CORRECTION (continued)
U.S. Pat. No. 7,595,331 B2

Column 34, Line 57, Claim 7:

After "and where any carbon of"

Delete: "CH₂ m" and insert: -- 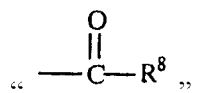 --.

Column 34, Lines 59-60, Claim 7:

After "substituted"

Delete:

" 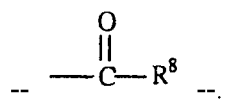 ".

Column 34, Line 65, Claim 7:

After "$C_{2\text{-}18}$ alkylene, or"

Insert:

-- 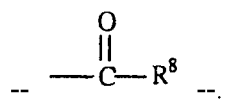 --.